US008789536B2

(12) United States Patent
Boyden et al.

(10) Patent No.: US 8,789,536 B2
(45) Date of Patent: Jul. 29, 2014

(54) MEDICAL OR VETERINARY DIGESTIVE TRACT UTILIZATION SYSTEMS AND METHODS

(75) Inventors: Edward S. Boyden, Cambridge, MA (US); Roderick A. Hyde, Redmond, WA (US); Muriel Y. Ishikawa, Livermore, CA (US); Jordin T. Kare, Seattle, WA (US); Robert Langer, Newton, MA (US); Eric C. Leuthardt, St. Louis, MO (US); Dennis J. Rivet, Portsmouth, VA (US); Michael A. Smith, Phoenix, AZ (US); Charles Whitmer, North Bend, WA (US); Lowell L. Wood, Jr., Bellewue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1259 days.

(21) Appl. No.: 11/998,152

(22) Filed: Nov. 27, 2007

(65) Prior Publication Data
US 2009/0104250 A1 Apr. 23, 2009

Related U.S. Application Data

(63) Continuation-in-part of application No. 11/982,448, filed on Oct. 31, 2007, and a continuation-in-part of application No. 11/975,371, filed on Oct. 17, 2007, now Pat. No. 8,038,659.

(51) Int. Cl.
| A61B 19/00 | (2006.01) |
| A61B 1/00 | (2006.01) |
| A61B 5/07 | (2006.01) |
| A61B 5/00 | (2006.01) |
| A61M 31/00 | (2006.01) |
| A61B 5/145 | (2006.01) |
| A61B 5/03 | (2006.01) |
| A61B 7/00 | (2006.01) |

(52) U.S. Cl.
CPC .......... *A61M 31/002* (2013.01); *A61B 5/14503* (2013.01); *A61B 5/073* (2013.01); *A61B 5/14532* (2013.01); *A61B 5/4839* (2013.01); *A61B 5/0008* (2013.01); *A61B 5/036* (2013.01); *A61B 5/14546* (2013.01); *A61B 5/076* (2013.01); *A61B 7/008* (2013.01); *A61B 5/42* (2013.01); *A61B 5/6882* (2013.01); *A61B 5/14539* (2013.01)
USPC ........................................................ 128/899

(58) Field of Classification Search
CPC .................. A61B 5/42–5/6873; A61B 5/6879; A61B 5/6882; A61B 5/6884; A61B 1/1041; A61B 1/00147; A61B 19/52–19/5244
USPC ........................................... 128/899; 600/114
See application file for complete search history.

(56) References Cited

U.S. PATENT DOCUMENTS

| 4,096,238 A | 6/1978 | Zaffaroni et al. |
| 4,207,890 A | 6/1980 | Mamajek et al. |
| 4,522,625 A | 6/1985 | Edgren |
| 4,595,583 A | 6/1986 | Eckenhoff et al. |
| 4,735,804 A | 4/1988 | Caldwell et al. |
| 4,758,436 A | 7/1988 | Caldwell et al. |
| 4,878,905 A * | 11/1989 | Blass ........................ 604/891.1 |
| 4,925,446 A | 5/1990 | Garay et al. |
| 5,198,229 A | 3/1993 | Wong et al. |
| 5,318,557 A | 6/1994 | Gross |
| 5,354,264 A | 10/1994 | Bae et al. |
| 5,576,025 A | 11/1996 | Akiyama et al. |
| 5,797,898 A | 8/1998 | Santini, Jr. et al. |
| 5,879,325 A | 3/1999 | Lindström et al. |
| 5,938,654 A | 8/1999 | Wong et al. |
| 6,120,803 A | 9/2000 | Wong et al. |
| 6,240,312 B1 | 5/2001 | Alfano et al. |
| 6,283,953 B1 | 9/2001 | Ayer et al. |
| 6,285,897 B1 * | 9/2001 | Kilcoyne et al. .............. 600/350 |
| 6,358,197 B1 | 3/2002 | Silverman et al. |
| 6,425,904 B1 | 7/2002 | Lemelson |
| 6,428,813 B1 | 8/2002 | Akiyama et al. |
| 6,475,521 B1 | 11/2002 | Timmins et al. |
| 6,535,764 B2 | 3/2003 | Imran et al. |
| 6,547,776 B1 | 4/2003 | Gaiser et al. |
| 6,582,720 B1 | 6/2003 | Inagi et al. |

| | | |
|---|---|---|
| 6,632,655 B1 | 10/2003 | Mehta et al. |
| 6,656,194 B1 | 12/2003 | Gannoe et al. |
| 6,656,464 B2 | 12/2003 | Kondo |
| 6,677,313 B1 | 1/2004 | Mathiowitz et al. |
| 6,689,056 B1 | 2/2004 | Kilcoyne et al. |
| 6,776,165 B2 | 8/2004 | Jin |
| 6,797,268 B2 | 9/2004 | Kodama et al. |
| 6,797,283 B1 | 9/2004 | Edgren et al. |
| 6,911,004 B2 | 6/2005 | Kim et al. |
| 6,929,636 B1 | 8/2005 | Von Alten |
| 6,939,290 B2 | 9/2005 | Iddan |
| 6,942,771 B1 | 9/2005 | Kayyem |
| 6,950,690 B1 | 9/2005 | Meron et al. |
| 6,958,034 B2 | 10/2005 | Iddan |
| 6,960,356 B1 | 11/2005 | Talwar et al. |
| 6,994,095 B1 | 2/2006 | Burnett |
| 7,016,735 B2 | 3/2006 | Imran et al. |
| 7,020,531 B1 | 3/2006 | Colliou et al. |
| 7,033,322 B2 | 4/2006 | Silver |
| 7,041,083 B2 | 5/2006 | Chu et al. |
| 7,083,578 B2 | 8/2006 | Lewkowicz et al. |
| 7,097,851 B1 | 8/2006 | Takada |
| 7,105,300 B2 | 9/2006 | Parce et al. |
| 7,105,810 B2 | 9/2006 | Kameoka et al. |
| 7,160,258 B2 | 1/2007 | Imran et al. |
| 7,182,957 B2 | 2/2007 | Zentner et al. |
| 7,220,237 B2 | 5/2007 | Gannoe et al. |
| 7,353,067 B1 | 4/2008 | Helland et al. |
| 7,654,985 B2 | 2/2010 | Dinsmoor et al. |
| 7,857,767 B2 | 12/2010 | Ferren et al. |
| 7,946,979 B2 * | 5/2011 | Gilad et al. .................. 600/109 |
| 8,038,659 B2 | 10/2011 | Boyden et al. |
| 2002/0012651 A1 | 1/2002 | Loeb |
| 2002/0055734 A1 | 5/2002 | Houzego et al. |
| 2002/0129443 A1 | 9/2002 | Di Cecco |
| 2002/0137803 A1 | 9/2002 | Kirkland |
| 2002/0151776 A1 | 10/2002 | Shawgo et al. |
| 2002/0173770 A1 * | 11/2002 | Flory et al. .................. 604/537 |
| 2003/0023150 A1 | 1/2003 | Yokoi et al. |
| 2003/0092964 A1 | 5/2003 | Kim et al. |
| 2003/0113371 A1 | 6/2003 | Dhawan et al. |
| 2003/0191476 A1 | 10/2003 | Smit |
| 2003/0216622 A1 | 11/2003 | Meron et al. |
| 2003/0232078 A1 | 12/2003 | Dong et al. |
| 2004/0109894 A1 | 6/2004 | Shefer et al. |
| 2004/0121015 A1 | 6/2004 | Chidlaw et al. |
| 2004/0158194 A1 | 8/2004 | Wolff et al. |
| 2004/0214311 A1 | 10/2004 | Levy |
| 2004/0220498 A1 | 11/2004 | Li et al. |
| 2004/0224019 A1 | 11/2004 | Shefer et al. |
| 2004/0236180 A1 | 11/2004 | Uchiyama et al. |
| 2004/0260346 A1 | 12/2004 | Overall et al. |
| 2005/0019407 A1 | 1/2005 | Sowden et al. |
| 2005/0037312 A1 | 2/2005 | Uchida |
| 2005/0058701 A1 * | 3/2005 | Gross et al. .................. 424/451 |
| 2005/0060030 A1 | 3/2005 | Lashinski et al. |
| 2005/0064027 A1 | 3/2005 | Jacob et al. |
| 2005/0065571 A1 | 3/2005 | Imran |
| 2005/0100937 A1 | 5/2005 | Holmes |
| 2005/0147559 A1 | 7/2005 | von Alten |
| 2005/0158246 A1 | 7/2005 | Takizawa et al. |
| 2005/0165272 A1 * | 7/2005 | Okada et al. .................. 600/114 |
| 2005/0201974 A1 | 9/2005 | Schestopol et al. |
| 2005/0222537 A1 | 10/2005 | Dinsmoor et al. |
| 2005/0234399 A1 | 10/2005 | Wood, Jr. |
| 2005/0245906 A1 | 11/2005 | Makower et al. |
| 2005/0246037 A1 | 11/2005 | Starkebaum |
| 2005/0249799 A1 | 11/2005 | Jacob et al. |
| 2005/0277912 A1 | 12/2005 | John |
| 2006/0003007 A1 | 1/2006 | Odidi et al. |
| 2006/0045865 A1 | 3/2006 | Jacob et al. |
| 2006/0062852 A1 | 3/2006 | Holmes |
| 2006/0063974 A1 | 3/2006 | Uchiyama et al. |
| 2006/0099245 A1 | 5/2006 | Kumar et al. |
| 2006/0152309 A1 | 7/2006 | Mintchev et al. |
| 2006/0157067 A1 | 7/2006 | Saadat et al. |
| 2006/0167339 A1 | 7/2006 | Gilad et al. |
| 2006/0182738 A1 | 8/2006 | Holmes |
| 2006/0190019 A1 | 8/2006 | Gannoe et al. |
| 2006/0195015 A1 | 8/2006 | Mullick et al. |
| 2006/0241718 A1 | 10/2006 | Tyler et al. |
| 2006/0248698 A1 | 11/2006 | Hanson et al. |
| 2006/0289640 A1 | 12/2006 | Mercure et al. |
| 2007/0080658 A1 | 4/2007 | Farritor et al. |
| 2007/0088334 A1 | 4/2007 | Hillis et al. |
| 2007/0106213 A1 | 5/2007 | Spera et al. |
| 2007/0106226 A1 | 5/2007 | Croll et al. |
| 2007/0123809 A1 | 5/2007 | Weiss et al. |
| 2007/0161851 A1 | 7/2007 | Takizawa et al. |
| 2007/0178160 A1 | 8/2007 | Burnett |
| 2007/0213659 A1 | 9/2007 | Trovato et al. |
| 2007/0219405 A1 | 9/2007 | Uchiyama et al. |
| 2007/0225576 A1 | 9/2007 | Brown et al. |
| 2007/0225633 A1 | 9/2007 | Ferren et al. |
| 2007/0244388 A1 | 10/2007 | Sato et al. |
| 2007/0253761 A1 | 11/2007 | May |
| 2007/0255100 A1 | 11/2007 | Barlow et al. |
| 2007/0265496 A1 | 11/2007 | Kawano et al. |
| 2008/0194912 A1 | 8/2008 | Trovato et al. |
| 2008/0214619 A1 | 9/2008 | Wolfe et al. |
| 2009/0306633 A1 | 12/2009 | Trovato et al. |

FOREIGN PATENT DOCUMENTS

| | | | |
|---|---|---|---|
| WO | WO 2006/077527 A1 | 7/2006 | |
| WO | WO 2006/077527 A2 | 7/2006 | |
| WO | WO 2007013059 A2 * | 2/2007 | ............... A61B 5/08 |

OTHER PUBLICATIONS

Duchene, D. et al.; "Pharaceutical and Medical Aspects of Bioadhesive Systems for Drug Administration"; Drug Development and Industrial Pharmacy; 1988; pp. 283-318; vol. 14, No. 2 & 3; Marcel Dekker, Inc.

Quirini, Marco et al.; "Design of a Pill-Sized 12-Legged Endoscopic Capsule Robot"; IEEE International Conference on Robotics and Automation in Rome, Italy; Apr. 10-14, 2007; pp. 1856-1862; vol. ThA7.2; IEEE.

Rentschler, Mark E. et al.; "Natural Orifice Surgery With an Endoluminal Mobile Robot"; SAGES Meeting; 2006; pp. 1-14; located at: http://robots.unl.edu/Files/Papers2/Rentschler_Natural_Orifice_Robot_with_figures.pdf.

Excerpt from The American Heritage Dictionary of the English Language; bearing a date of 2009; Printed on Jan. 19, 2011; located at: http://education.yahoo.com/reference/dictionary/entry/moor; total of 2 pages.

* cited by examiner

*Primary Examiner* — Charles A Marmor, II
*Assistant Examiner* — Catherine B Kuhlman

(57) ABSTRACT

Systems and methods are described for implementing or deploying medical or veterinary utility modules (a) operable for mooring at least partly within a digestive tract, (b) small enough to pass through the tract per vias naturales and including a wireless-control component, (c) having one or more attachment protrusions positionable adjacent to a mucous membrane, (d) configured to facilitate redundant modes of attachment, (e) facilitating a "primary" material supply deployable within a stomach for an extended and/or controllable period, (f) moored by one or more adaptable extender modules supported by a subject's head or neck, and/or (g) configured to facilitate supporting at least a sensor within a subject's body lumen for up to a day or more.

20 Claims, 19 Drawing Sheets

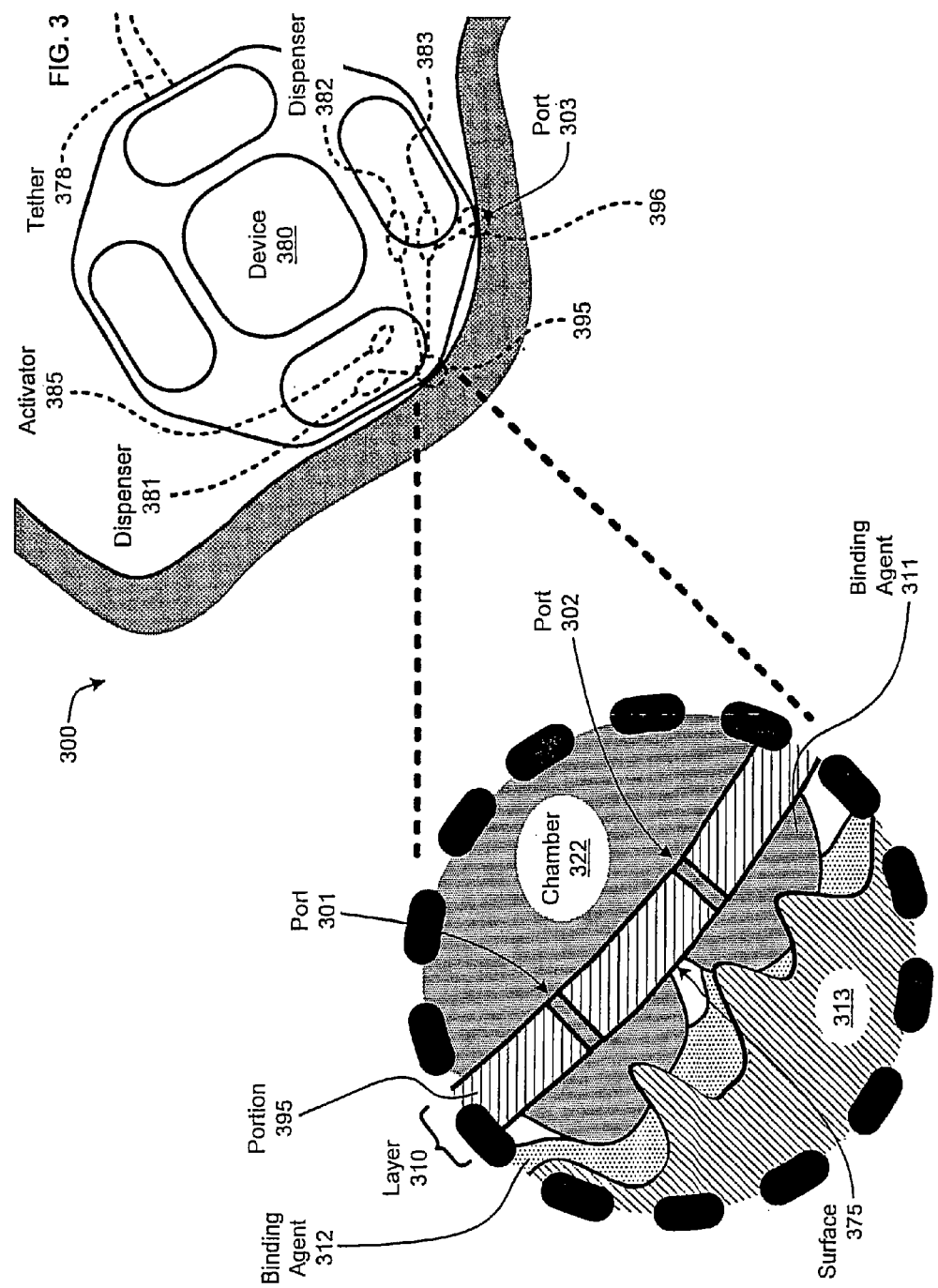

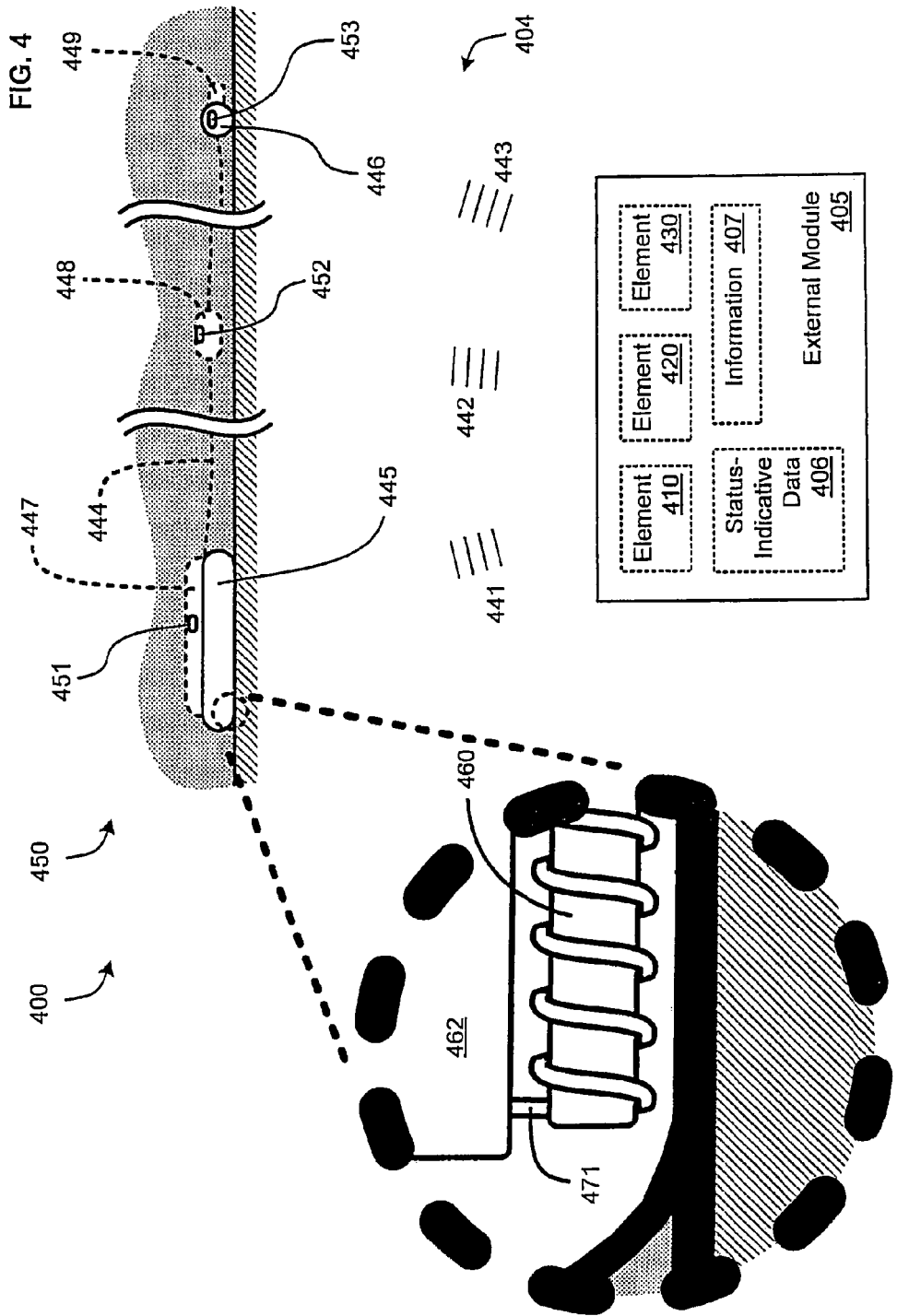

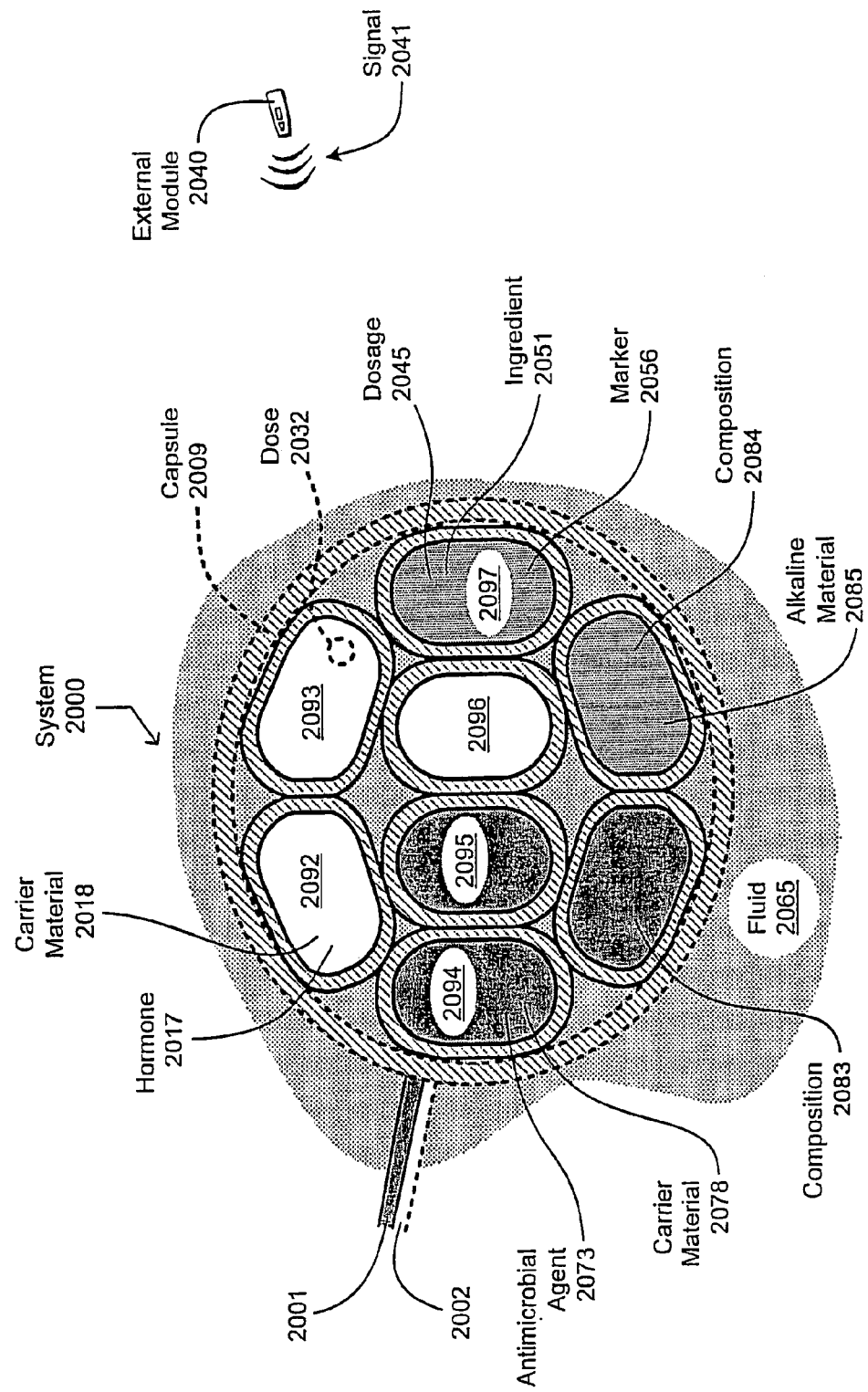

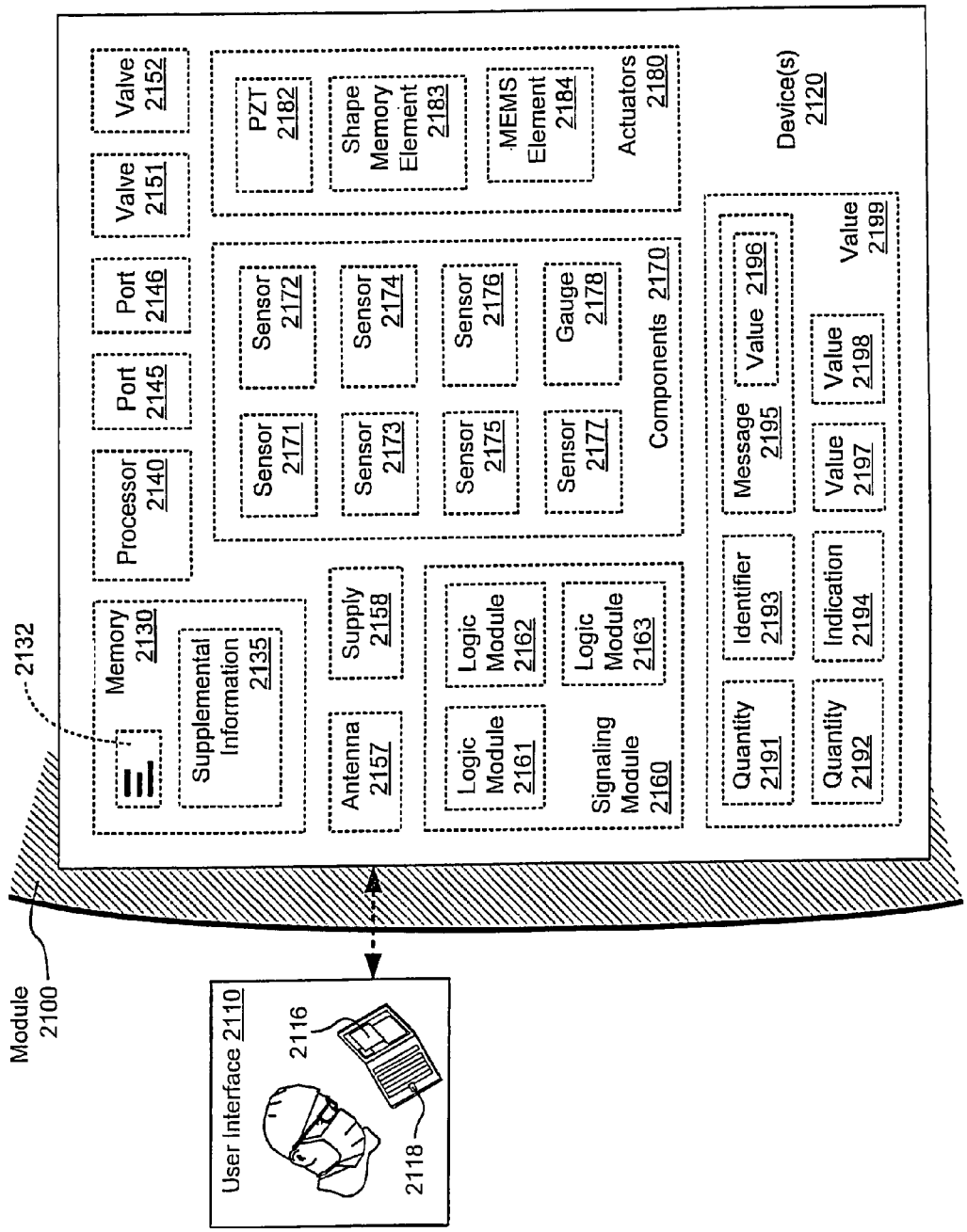

MEDICAL OR VETERINARY DIGESTIVE TRACT UTILIZATION SYSTEMS AND METHODS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/982,448, entitled MEDICAL OR VETERINARY DIGESTIVE TRACT UTILIZATION SYSTEMS AND METHODS, naming Edward S. Boyden, Roderick A.; Hyde, Muriel Y. Ishikawa, Jordin T. Kare, Robert Langer, Eric C. Leuthardt, Dennis J. Rivet, Michael A. Smith, Charles Whitmer, Lowell L. Wood, Jr. and Victoria Y. H. Wood as inventors, filed 31 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/975,371, entitled DISINTEGRATING DIGESTIVE TRACT INTERACTION SYSTEM, naming Edward S. Boyden, Roderick A.; Hyde, Muriel Y. Ishikawa, Jordin T. Kare, Robert Langer, Eric C. Leuthardt, Dennis J. Rivet, Michael A. Smith, Charles Whitmer, Lowell L. Wood, Jr. and Victoria Y. H. Wood as inventors, filed 17 Oct. 2007 now U.S. Pat. No. 8,038,659, which is currently co-pending, or is an application of which a currently co-pending application is entitled to the benefit of the filing date. For purposes of the USPTO extra-statutory requirements, the present application constitutes a continuation-in-part of U.S. patent application Ser. No. 10/536,126, entitled ADAPTIVE DISPENSATION IN A DIGESTIVE TRACT, naming Edward S. Boyden, Roderick A.; Hyde, Muriel Y. Ishikawa, Jordin T. Kare, Robert Langer, Eric C. Leuthardt, Dennis J. Rivet, Michael A. Smith, Charles Whitmer, Lowell L. Wood, Jr. and Victoria Y. H. Wood as inventors, filed 23 Oct. 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a system includes but is not limited to a medical or veterinary utility module small enough to pass through a digestive tract per vias naturales, the medical or veterinary utility module including at least a wireless-control component having at least an engaging state and a disengaging state, the engaging state operable to cause the medical or veterinary utility module at least to remain within a portion of the digestive tract, the disengaging state allowing the medical or veterinary utility module to exit the digestive tract per vias naturales. In addition to the foregoing, other system aspects are described in the claims, drawings, and text forming a part of the present disclosure.

In one aspect, a system includes but is not limited to a protruding surface narrow enough to be positioned adjacent to a mucous membrane; a first binding agent secretion port operable for binding at least to a first portion of the protruding surface; and a second binding agent secretion port operable for binding at least to a first portion of the mucous membrane. In addition to the foregoing, other system aspects are described in the claims, drawings, and text forming a part of the present disclosure.

In one aspect, a system includes but is not limited to a module body small enough for a subject to swallow; an earlier-acting attachment feature operable for coupling the module body to a first portion of a mucous membrane; and a later-acting attachment feature operable for initially coupling the module body to a second portion of the mucous membrane at least one minute after the earlier-acting attachment feature initially couples the module body to the first portion of the mucous membrane. In addition to the foregoing, other system aspects are described in the claims, drawings, and text forming a part of the present disclosure.

In one aspect, a system includes but is not limited to a medical or veterinary utility module; and one or more adaptable extender modules operable to provide support for the medical or veterinary utility module at one or more cranial or throat positions within a subject. In addition to the foregoing, other system aspects are described in the claims, drawings, and text forming a part of the present disclosure.

In one aspect, a system includes but is not limited to a primary material supply operable for placement within a stomach; and one or more conduits operable to guide material from the primary material supply out of the stomach. In addition to the foregoing, other system aspects are described in the claims, drawings, and text forming a part of the present disclosure.

In one aspect, a system includes but is not limited to one or more sensor-containing modules each small enough to pass through a digestive tract; a mooring module operable to remain in the digestive tract for more than a day; and one or more tethers configured to establish an effective range of motion of the one or more sensor-containing modules relative to the mooring module within the digestive tract. In addition to the foregoing, other system aspects are described in the claims, drawings, and text forming a part of the present disclosure.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIGS. 3-25 depict respective contexts in which one or more medical or veterinary technologies as described herein may be implemented.

DETAILED DESCRIPTION

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In the following detailed description, reference is made to the accompanying drawings, which form a part hereof. The use of the same symbols in different drawings typically indicates similar or identical items. The illustrative embodiments described in the detailed description, drawings, and claims are not meant to be limiting. Other embodiments may be utilized, and other changes may be made, without departing from the spirit or scope of the subject matter presented here.

Figure 1:
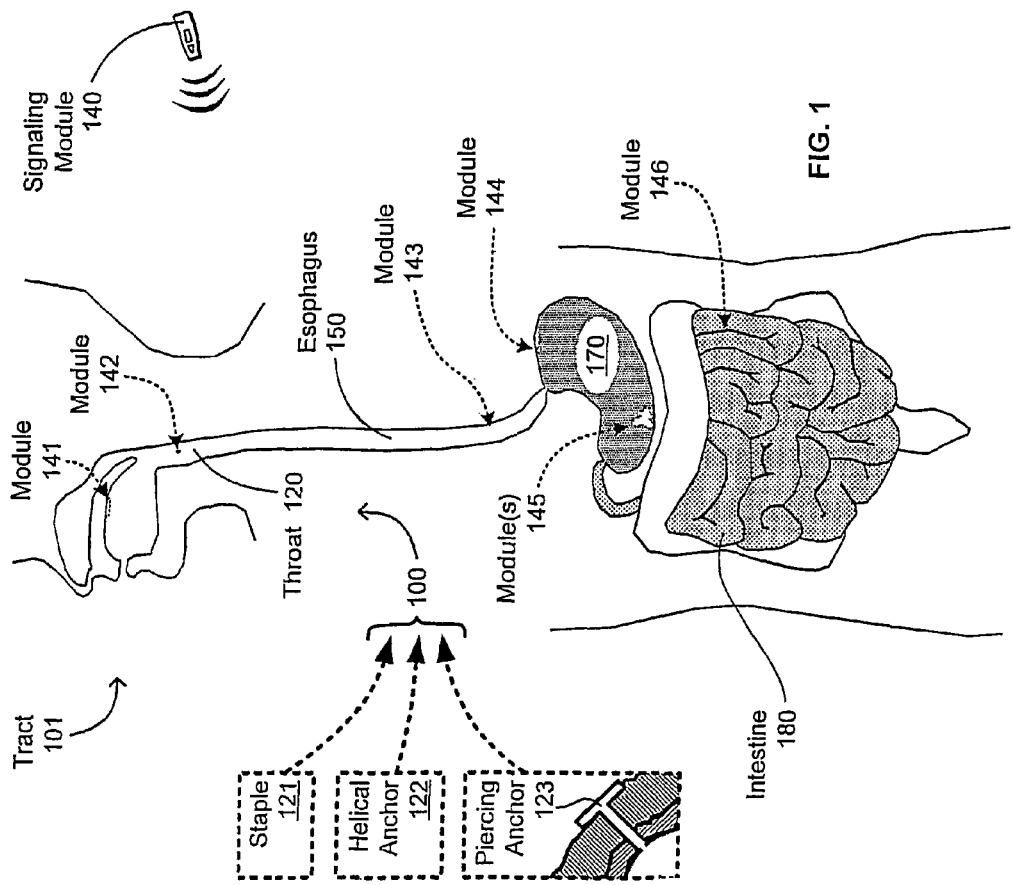
FIG. 1 depicts an exemplary environment in which one or more technologies may be implemented.

With reference now to FIG. 1, shown is a system 100 in which one or more technologies may be implemented. System 100 may include one or more utility modules 141, 142, 143, 144, 145, 146 positioned along digestive tract 101. In some contexts, such utility modules 141-146 may be supported directly or indirectly by one or more surgical staples 121, helical anchors 122, other piercing anchors 123, bioadhesives, or other such durable modes of attachment for controllable and/or extended functionality. Such bioadhesives, in some embodiments, may comprise a mixture of poloxamer 407 with polycarbophil, or some similar gel-forming liquid. Other such liquid-based bioadhesives may include, for example, polycarbophil or polyacrylic acid secreted via one or more ports of a utility or mooring module as described herein.

Figure 7:
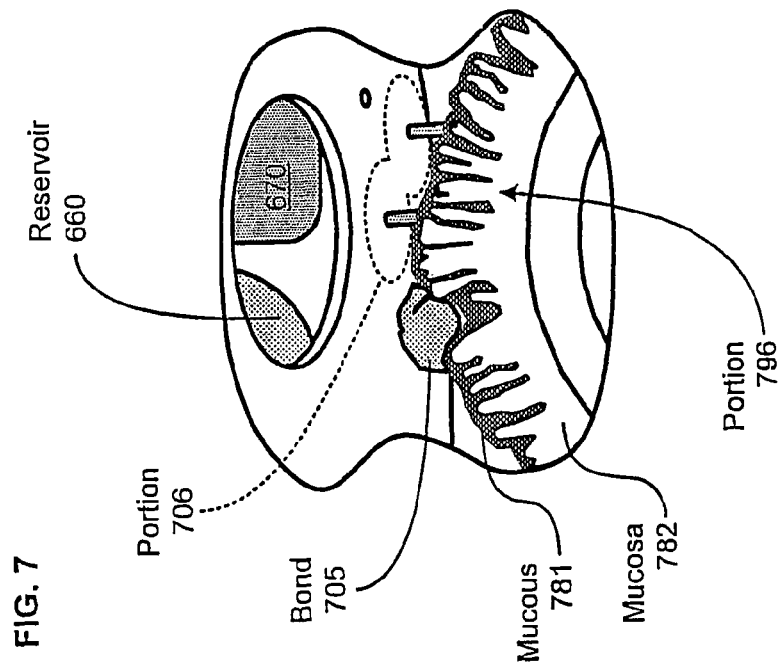

In some embodiments, one or more such utility modules 141-146 are small enough to pass through digestive tract 101 per vias naturales, and include at least a wireless-control component responsive to signaling module 140. See, e.g., FIG. 2. Alternatively or additionally, any such utility modules 141-146 and/or mooring modules thereof may, in some variants, include a body with a protruding surface narrow enough to be positioned adjacent to a mucous membrane. See, e.g., FIG. 3. Alternatively or additionally, any such utility modules 141-146 and/or mooring modules thereof may, in some variants, be configured with more than one adhesive or other attachment feature so as to facilitate sequential or otherwise redundant modes of attachment. See, e.g., FIGS. 5-7. Alternatively or additionally, any such utility modules 141-146 and/or mooring modules thereof may, in some variants, be configured to facilitate a "primary" material supply deployable within gastric compartment 170 for an extended and/or controllable period, but operable for dispensing elsewhere. See, e.g., FIG. 8. Alternatively or additionally, any such mooring modules may comprise adaptable extender module at least partly supported by a subject's head or neck, for facilitating an extended or controllable placement of one or more such utility modules 141-146. Alternatively or additionally, one or more such sensor-containing utility modules 142-146 may be tethered or otherwise moored so as to remain in a specific portion of a subject's throat 120, esophagus 150, gastric compartment 170, or intestine 180 for up to a day or more. In some variants, moreover, any of the herein-described modules may likewise be configured to include one or more wireless-control components for use in response to or otherwise in cooperation with a signaling module 140 operable for wireless communication. See, e.g., U.S. patent application Ser. No. 10/536,126, titled "Adaptive Dispendsation in a Digestive Tract, filed 23 Oct. 2007, also by Boyden et al., incorporated by reference to the extent not inconsistent herewith.

Figure 2:
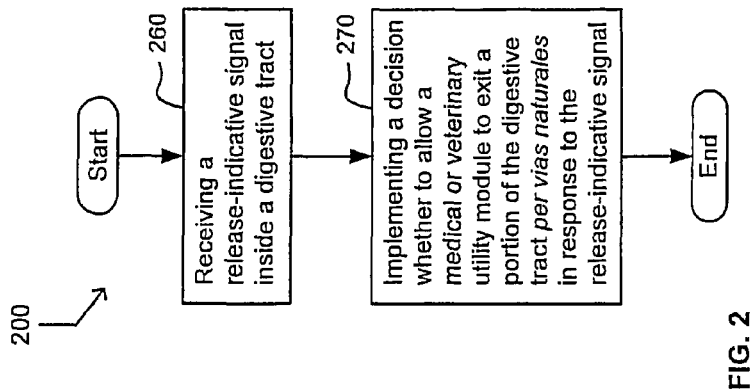
FIG. 2 depicts a high-level logic flow of an operational process.

With reference now to FIG. 2, shown is a flow 200 comprising operation 260—receiving a release-indicative signal inside a digestive tract—and operation 270—implementing a decision whether to allow a medical or veterinary utility module to exit a portion of the digestive tract per vias naturales in response to the release-indicative signal. In various embodiments, one or more utility modules 141-146 described above and/or mooring modules thereof may perform flow 200 so as to permit one or more utility modules 141-146 to be removed from tract 101 passively, or to advance controllably along it to successive positions as described herein.

With reference now to FIG. 3, shown is a medical or veterinary system 300 in which one or more technologies may be implemented. System 300 may include one or more mooring modules or other devices 380 having a protruding surface 375 narrow enough to be positioned adjacent to a portion 395 of a mucous membrane 313, a first secretion port 301 (from dispenser 381, for example) operable for binding at least to a portion 395 of the protruding surface 375 of layer 310 as shown; and at least one other secretion port 302 (at least from dispenser 383 via chamber 322, for example) operable for binding at least to the adjacent portion 395 of the mucous membrane 313. In some variants, as shown, one or more binding agents 312 secreted via at least the second secretion port 302 also bind to another binding agent 311, directly to mucosa, or to other structures described herein. Alternatively or additionally, device 380 may include one or more other dispensers 382, magnetic or other flux-guiding elements, one or more activators 385 (using heat or light to activate a binding agent, for example), or tethers 378 or other supported structures as described herein. In some variants, device 380 may likewise include one or more other protruding surfaces 375 narrow enough to be positioned adjacent to another portion 396 of the mucous membrane 313, optionally having one or more other ports 303 operable for facilitating adhesion therebetween. Such adhesives may include surgical adhesive such as cyanoacrylates or their derivatives, or any other sufficiently adhesive compound (with sufficiently low toxicity to intra-luminal cells) for a specified observational and/or therapeutic interval. Other suitable binding agents may include fibrin glues, any number of glues based on collagen or gelatin, or other such biologically mediated binding agents. Still others may comprise one or more erodible polymers selected from the group consisting of soluble cellulosic materials, ethylene vinyl alcohol, ethylene maleic anhydride copolymer, polyacrylates, polycaprolactones, inorganic glass based on polyphosphates and fused salts, polyanhydrides, poly (ortho)esters, biodegradable polyurethanes, polyvinyl pyrrolidone, polyactones, polyamides and polypeptides, gelatin and derivatives, polyacrylonitriles, polyesters, and combinations thereof.

With reference now to FIG. 4, shown is a system 400 in which one or more technologies may be implemented. A digestive tract portion 404 is shown with medical or veterinary utility modules 447, 448, 449, 450 (individually or collectively) small enough to pass through the digestive tract safely per vias naturales. Such modules 447-450 may each include one or more wireless-control components 451, 452, 453. At least one such component has one or more engaging states and one or more disengaging states. The engaging state(s) cause(s) the medical or veterinary utility module to remain stationary, or at least to remain within digestive tract portion 404 for a controllable and/or extended period, using one or more techniques as described herein. The disengaging state(s) allow(s) the medical or veterinary utility module to exit the digestive tract per vias naturales.

In some variants one or more instances of external modules 405 (outside the digestive tract) may be used for monitoring or guiding the behavior of one or more such utility modules 447-450. External module 405 may include one or more instances of optical communication elements 410, radio frequency communication elements 420, magnetic-field-generating elements 430, or magnetic materials or other such components that may be effective for interacting with the utility module(s) 447-450.

In some contexts, one or more optical communication elements 410 may be operable to transmit one or more wireless signals 441 comprising instructions and/or other information to component 451, for example, via a subject's mouth or other optically accessible site. Alternatively or additionally, component 451 may likewise be configured to transmit status-indicative data 406 or other such information 407 wirelessly to external module 405. In some contexts, one or more radio frequency communication elements 420 may likewise be operable to transmit one or more wireless signals 442 comprising instructions and/or other information to component 452, for example. Alternatively or additionally, component 451 may likewise be configured to transmit status-indicative data 406 or other such information 407 as wireless signals 442 to external module 405. In some contexts, one or more magnetic-field-generating or other elements 430 may likewise be operable to transmit one or more wireless signals 443 comprising instructions and/or other information to component 453, for example. Alternatively or additionally, component 453 may likewise be configured to transmit status-indicative data 406 or other such information 407 as wireless signals 443 to external module 405.

In some variants, (component or other) mooring modules 445, 446 may be adhesively, magnetically, buoyantly, spatially, or otherwise operable to remain in digestive tract portion 404 for a month, a year, or longer. Such mooring modules may provide a convenient site for supporting one or more utility modules 447-450 directly and/or by an interstitial structure such as one or more tethers 444. Such support may be appropriate, in some contexts, for a day, a week, or more, as described herein.

One or more utility modules 447-450, for example, may be magnetically or otherwise supported by one or more mooring component modules 451 having a length more than four times greater than its median width. Such a magnetic configuration may, for example, include one or more ferromagnetic elements 460 operable for magnetic coupling with a high power electromagnet or other external flux-guiding structure adjacent digestive tract portion 404, a ferromagnet worn on a belt, an implanted implanted material surrounding the pylorus, or some other nearby structure outside the digestive tract. Removing such a belt may, for example, permit a user to cause ferromagnetic element 460 to be released per vias naturales, for example. Alternatively or additionally, mooring module 445 and/or one or more utility modules 447-450 may be released by current source 462 generating a current in one or more conductive coils 471 at least partly in opposition to the magnetic field generated by the ferromagnetic element(s) 460. A similar effect can be achieved by various flux-manipulation techniques, in lieu of or in addition to such current, such by moving oppositely-oriented ferromagnets (down as shown) into proximity with the depicted wall of digestive tract portion 404. Alternatively or additionally, inflation or other modes of actuation may be used to achieve a disengagement of the utility module(s) 447-450. For examples of releasable tethering implementations, for example, see FIGS. 8-11 & 13-18 and their descriptions below.

Some variants of system 400 may be characterized as a medical or veterinary system comprising one or more sensor-containing modules, one or more mooring modules 445, 446 operable to remain within portion 404 for more than a day; and one or more tethers 444 configured to establish an effective range of motion of the one or more sensor-containing modules relative to the mooring module(s) within the digestive tract comprising portion 404. This can occur, for example, in a context in which the contained sensor(s) implement one or more features described below with reference to FIG. 21 or 23 and in which the sensor-containing module(s) are implemented as one or more instances of utility modules 448 small enough to pass (safely) through a digestive tract. Alternatively or additionally, one or more mooring modules 445 may likewise include one or more physical measurement components used by or with such sensors.

Figure 5:
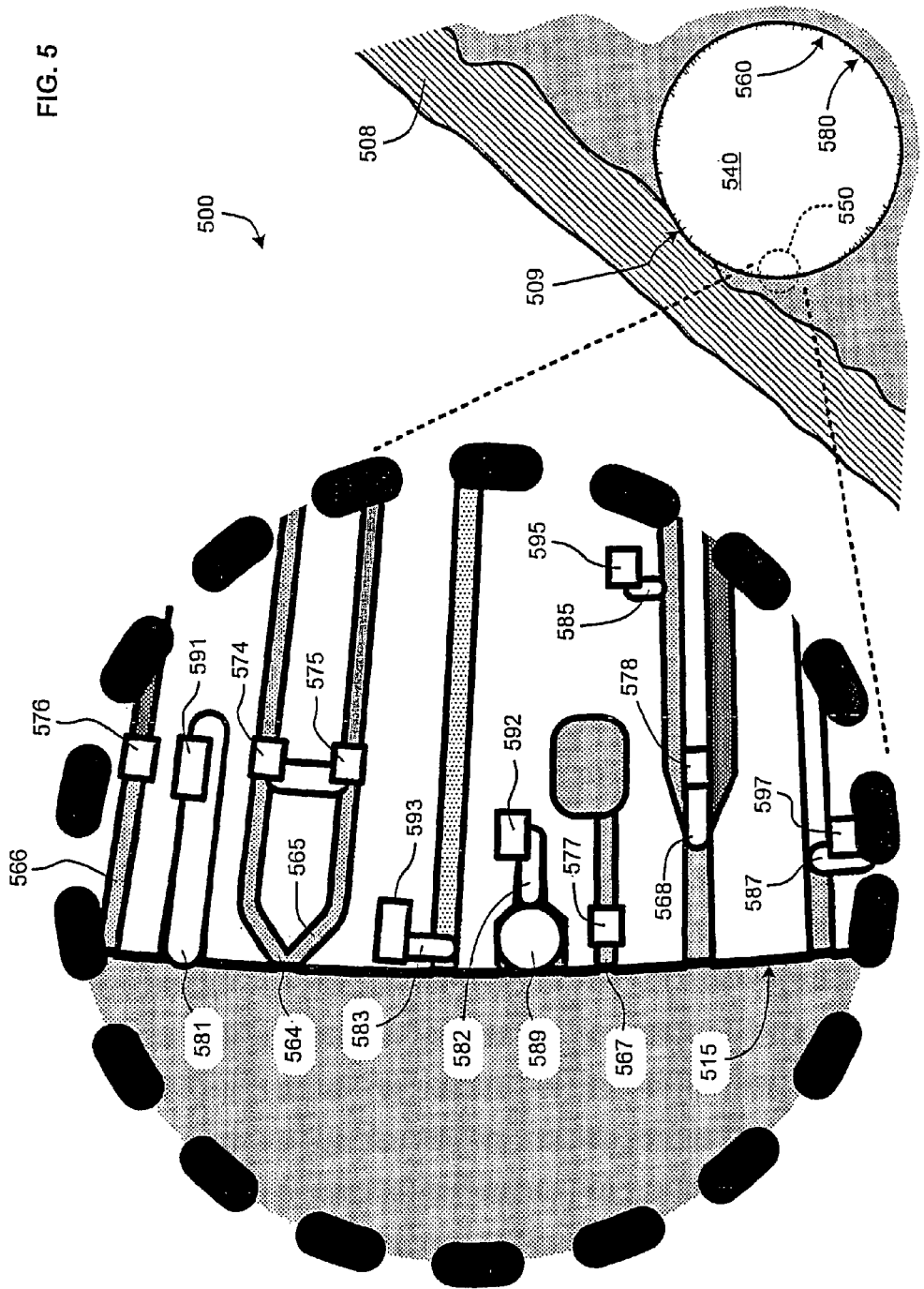

With reference now to FIG. 5, shown is another system 500 operable for retaining one or more medical or veterinary utility modules in a digestive tract for an extended and/or controlled period. System 500 may comprise one or more instances of a mooring and/or utility module 540 having a protruding surface 515 immersed so that a portion 509 thereof is adjacent an irregular mucous membrane 508 of a digestive tract. System 500 may (optionally) comprise one or more control components 550 such as one or more instances of adhesive-containing dispensers 564 and control circuitry 574 therefor, adhesive-solvent-containing dispenser 565 and control circuitry 575 therefor, anticoagulant-agent-containing dispenser 566 and control circuitry 576 therefor, antibiotic-containing dispenser 567 and control circuitry 577 therefor, or hybrid dispenser 568 and control circuitry 578 therefor. Alternatively or additionally, the control component(s) 550 may likewise comprise one or more instances of disengagement-inducing actuator 581 and control circuitry 591 therefor, releasable dispenser 589, dispenser-releasing actuator 582 and control circuitry 592 therefor, reservoir-opening actuator 583 and control circuitry 593 therefor, dosage-adjustment actuator 585 and control circuitry 595 therefor, or hybrid actuator 587 and control circuitry 597 therefor. Alternatively or additionally, the control component(s) 550 may be similarly configured to control one or more selected dispensers 560 or other actuators 580. Alternatively or additionally, the control component(s) 550 may likewise be configured to perform one or more other functions wirelessly, such as those described with reference to utility module 450 of FIG. 4 or elsewhere herein. Hybrid dispenser 568 and dosage-adjustment actuator 585 may likewise be configured for access to any of the materials or reservoirs described with reference to FIG. 20 herein, for example. In some variants, moreover, external module 405 may be operative for updating such control circuitry 591-595 wirelessly or otherwise as described herein, optionally commencing or altering one or more criteria for module 540 the digestive tract per vias naturales.

In light of these teachings, numerous existing techniques may be applied for using biologically compatible binding agents as described herein without undue experimentation. See, e.g., U.S. Pat. No. 7,265,098 ("Polyacid/polyalkylene oxide gels and methods for their delivery"); U.S. Pat. No. 7,255,874 ("Biocompatible polymers and adhesives: compositions, methods of making and uses related thereto"); U.S. Pat. No. 7,097,851 ("Oral formulation for gastrointestinal drug delivery"); U.S. Pat. No. 7,056,550 ("Medical devices, drug coatings and methods for maintaining the drug coatings thereon"); U.S. Pat. No. 6,800,296 ("Modification of surfaces using biological recognition events"); U.S. Pat. No. 6,764,696 ("Effervescent drug delivery system for oral administration"); U.S. Pat. No. 6,689,380 ("Remote and local controlled delivery of pharmaceutical compounds using electromagnetic energy"); U.S. Pat. No. 6,582,720 ("Medicinal compositions adhering to stomach/duodenum"); U.S. Pat. No. 6,576,712 ("Preparation of hydrophilic pressure sensitive adhesives having optimized adhesive properties"); U.S. Pat. No. 6,428,813 ("Gastrointestinal mucosa-adherent pharmaceutical composition"). Those skilled in the art will also recognize how to apply numerous existing techniques for taking provisional, alternate, overlapping, or completion actions relating to such applications as exemplified herein without undue experimentation, in light of these teachings. Binding agents may likewise be used for coupling modules as described herein, before or during deployment.

Figure 6:
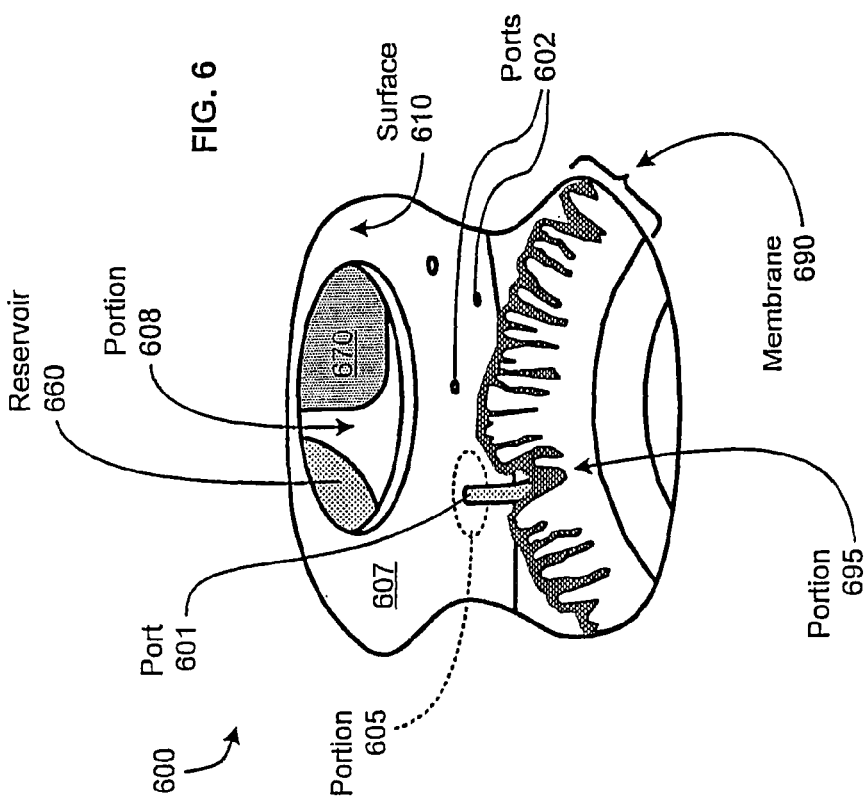

With reference now to FIG. 6, shown is another context in which one or more technologies may be implemented. A medical or veterinary system 600 shown there comprises at least one module body 607 small enough for a person or other subject to swallow. System 600 further comprises one or more (earlier-acting) ports 601 operable for dispensing adhesive-containing material from reservoir 660 and/or otherwise coupling at least portion 605 of module body 607 to a portion 695 mucous membrane 690. (As shown, surface 610 includes a portion 608 cut away to reveal a plurality of adhesive-containing reservoirs 660, 670.)

Some time later—such as an hour or a day, in some context—one or more other (ports 602 or other) attachment features may be invoked for coupling at least the module body 607 to another part of the mucous membrane 690. In a context in which bond 705 is formed within a minute at portion 605, for example, another application of adhesive may be dispensed (from reservoir 670 via ports 602, for example), bonding another portion 706 of module body 607 to another portion 796 of the mucous membrane 690. In some variants, for example, such sequential attachment operations may permit improved coupling with mucous 781 and/or mucosa 782.

Various modes of sequential attachment may be practiced, for example, in the context of FIG. 5. In a context in which module 540 is small enough to swallow, for example, it may initially attach to a mucous membrane 508 of an esophagus, gastric compartment, or intestine as shown. This can be accomplished by hooks or ligation components, for example, or by an activation of one or more adhesive-containing dispensers 564 (at least adjacent mucous membrane 508) by corresponding control circuitry 574. In some variants, for example, control circuitry 591 responsive to one or more sensors (optionally a piezoelectric transducer or other proximity- or contact-sense-enabled component, for example) may trigger one or more adjacent or successive dispensers to dispense an adhesive, for example.

Some time later, perhaps on the order of 10 minutes or 10 hours, one or more "next" adhesive or other attachment features are likewise invoked to attach (a) at a deeper level of mucous membrane 508 and/or (b) to a next vertical or lateral portion of mucous membrane 508. In the latter case, for example, module 540 may advance very slowly along mucous membrane 508, such as by rolling. In response to detecting a (wireless or other) disengagement-indicative condition, in some embodiments, module 540 may be configured to respond by ceasing such attachment operations, by invoking control circuitry 575 to activate adhesive-solvent-containing dispenser 565, by invoking control circuitry 591 to activate disengagement-inducing actuator 581 to push mucous membrane 508 away from module 540, or otherwise by facilitating detachment. Alternatively or additionally, such modes may include separating tether portions, adjusting buoyancy, activating a pressurized or other mode of propulsion, exerting tension along a moored tether, or other actions as described herein.

Figure 8:
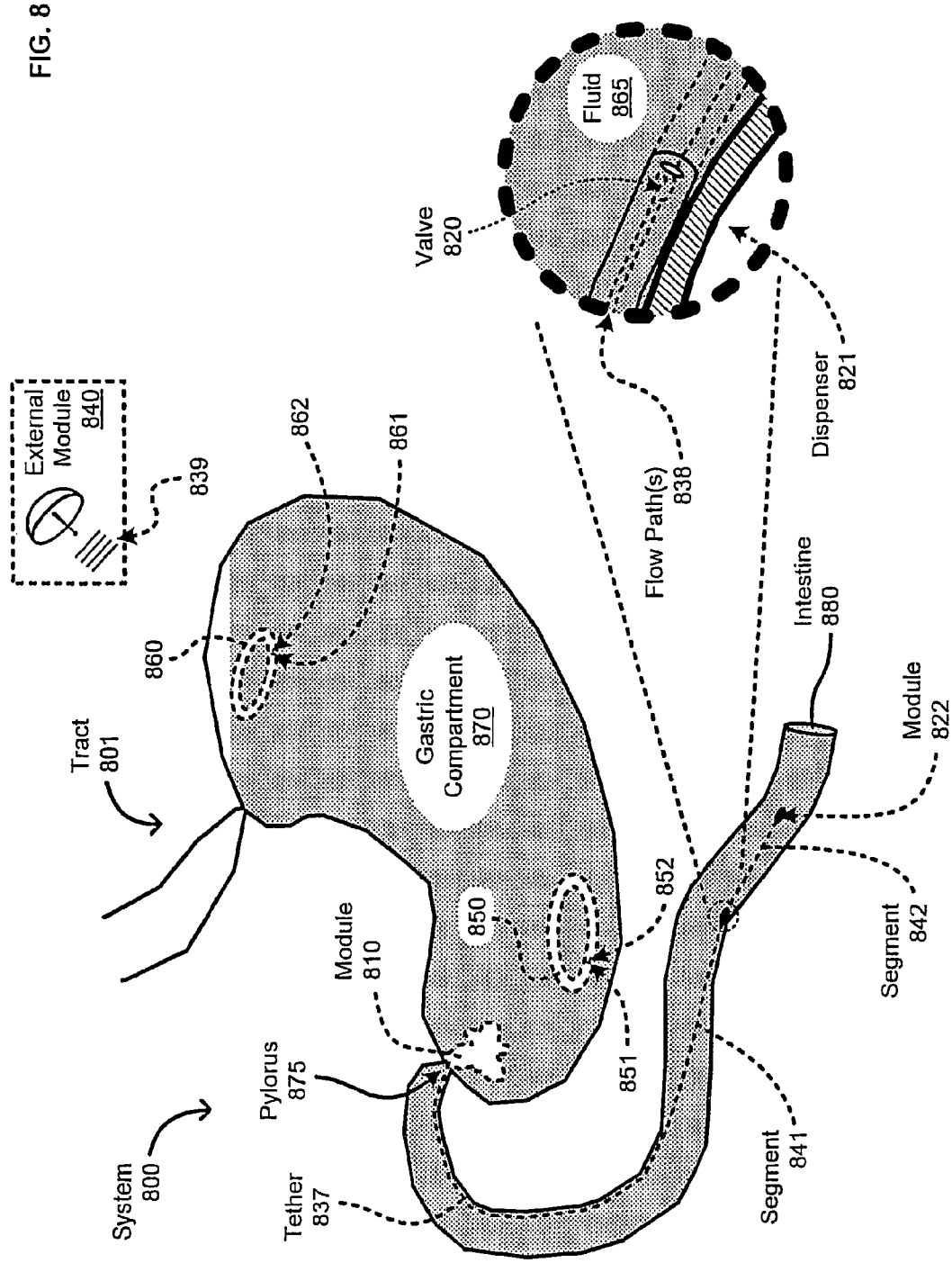

With reference now to FIG. 8, shown is a vicinity of a gastric compartment 870 in a digestive tract 801 of a subject (human or otherwise) that may serve as a context for introducing one or more processes and/or devices described herein. As shown system 800 may (optionally) include one or more instances of module 810 each having one or more tethers 837 or other portions extending through some of intestine 880 and configured to anchor at pylorus 875. System 800 may likewise include one or more instances of modules 850 dense enough to rest near the bottom of gastric compartment 870 and/or modules 860 buoyant enough to float within gastric compartment 870, any or all of which may be configured with one or more dispensers 851, 861 and/or control modules 852, 862. Many suitable structures are described herein and in U.S. patent application Ser. No. 11/975,371, titled "Disintegrating Digestive Tract Interaction System," filed 17 Oct. 2007, issued as U.S. Pat. No. 8,038,659, also by Boyden et al., incorporated by reference to the extent not inconsistent herewith. In some such embodiments, each tether 837 of interest may comprise one or more segments 841 directly or indirectly coupling a reservoir-containing module (such as module 810 or module 850) with one or more of its dispensers 821. In some variants, moreover, such modules 810, 850, 860 may comprise control modules 852, 862 or other circuitry operable for handling one or more wireless signals 839 passing to or from external module 840. Alternatively or additionally, each tether 837 of interest may comprise one or more segments 842 directly or indirectly coupling a reservoir-containing module with one or more of its sense modules 822. In various embodiments described herein, such dispensers, sensor modules, and support structures therefore may each be inside, outside, or spanning the gastric compartment or, in some cases, extending outside the digestive tract. In some variants, one or more such segments 841, 842 configured to support such devices in intestine 880 comprise structures of a (positive) solubility in a gastric compartment low enough to remain in situ for more than a day (or month or year), as described herein. Alternatively or additionally one or more such modules 810, 850, 860 may include two or more (component) modules similarly tethered together as described herein.

In some embodiments, one or more such modules 810, 850, 860 or other fluid-exposed structures depicted herein may comprise at least an external layer primarily made of one or more water insoluble polymers such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such low-solubility elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 3 to 30 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents or other soluble structures for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release responsive to ingestion.

In some embodiments, one or more therapeutic agents or other structures may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048,945; 7,056,951; hereby incorporated by reference to the extent not inconsistent herewith).

Some variants of system 800 may be characterized as medical or veterinary systems comprising one or more material supplies in module 810 operable for placement within a stomach (gastric compartment 870) and operably coupled with one or more conduits in tether 837 to guide material from the module 810 out of the stomach. Many reservoir-containing structures described herein are well suited for such transgastric dispensations of therapeutic or other agents. See FIGS. 10 & 13-22. In light of teachings herein, numerous existing techniques may be applied for preparing appropriate such drug delivery formulations, as described herein, without undue experimentation. See, e.g., U.S. Pat. No. 7,189,414 ("Controlled release oral drug delivery system"); U.S. Pat. No. 7,125,566 ("Particulate drug-containing products and method of manufacture"); U.S. Pat. No. 7,097,851 ("Oral formulation for gastrointestinal drug delivery"); U.S. Pat. No. 6,960,356 ("Orally administered drug delivery system providing temporal and spatial control"); U.S. Pat. No. 6,699,503 ("Hydrogel-forming sustained-release preparation"); U.S. Pat. No. 6,644,517 ("Stem configuration to reduce seal abrasion in metered dose aerosol valves"); U.S. Pat. No. 6,638,534 ("Preparation capable of releasing drug at target site in intestine"); U.S. Pat. No. 6,582,720 ("Medicinal compositions adhering to stomach/duodenum"); U.S. Pat. No. 6,475,521 ("Biphasic controlled release delivery system for high solubility pharmaceuticals and method"); U.S. Pat. No. 6,399,086 ("Pharmaceutical preparations for the controlled release of beta-lactam antibiotics"); U.S. Pat. No. 6,240,917 ("Aerosol holding chamber for a metered-dose inhaler"); U.S. Pat. No. 6,116,237 ("Methods of dry powder inhalation"); U.S. Pat. No. 6,060,069 ("Pulmonary delivery of pharmaceuticals"); U.S. Pat. No. 5,989,217 ("Medicine administering device for nasal cavities"); U.S. Pat. No. 5,906,587 ("Apparatus and method for the treatment of esophageal varices and mucosal neoplasms"); U.S. Pat. No. 5,837,261 ("Viral vaccines"); U.S. Pat. No. 5,823,180 ("Methods for treating pulmonary vasoconstriction and asthma"); U.S. Pat. No. 5,645,051 ("Unit dose dry powder inhaler"). Those skilled in the art will also recognize how to apply numerous existing techniques for taking provisional, alternate, overlapping, or completion actions relating to such applications as exemplified herein without undue experimentation, in light of these teachings. One or more wireless signals 839 may be used directly to control some or all aspects of activating one or more such dispensers 821, 861 on a selective basis, for example. Sense module 822 may be configured to signal one or more dispensers 821, 851 to reduce, postpone, or forego an output of a bioactive material, for example, in response to a high level of such materials (or metabolites or other indicators thereof) being detected. Alternatively or additionally, such functionality may be configured to depend on whether one or more modules 810, 850, 860 are depleted, not yet deployed, disintegrated, or in some other condition that may prevent effective operation.

In some cases, such functionality may likewise depend upon one or more other determinants in substantially any desired combination: upon whether excessive acidity or some other symptom has been detected directly, upon whether an a priori attribute of a subject makes a bioactive material unnecessary and/or unsafe for a potential dispensation, upon whether the subject has contemporaneously requested or otherwise authorized a pain reliever, upon how long a time has elapsed since a prior dispensation, upon other state or timing factors as described herein, upon how much remains of a reservoir or other bioactive material supply, upon whether a subject has taken alcohol or any other controlled substance, or upon other determinants such as are known in the art. Such combinations may each be effectuated by comparative, arithmetic, conjunctive, or other operators relating each pairing of determinants described herein, for example.

In light of these teachings, numerous existing techniques may be applied for performing appropriate telemetry or otherwise handling wireless signals as described herein without undue experimentation. See, e.g., U.S. Pat. No. 7,262,020 ("Methods for comparing relative flux rates of two or more biological molecules in vivo through a single protocol"); U.S. Pat. No. 7,214,182 ("Wireless in-vivo information acquiring system, body-insertable device, and external device"); U.S. Pat. No. 7,160,258 ("Capsule and method for treating or diagnosing the intestinal tract"); U.S. Pat. No. 7,146,216 ("Implantable muscle stimulation device for treating gastrointestinal reflux disease"); U.S. Pat. No. 7,118,529 ("Method and apparatus for transmitting non-image information via an image sensor in an in vivo imaging system"); U.S. Pat. No. 6,929,636 ("Internal drug dispenser capsule medical device"); U.S. Pat. No. 6,632,655 ("Manipulation of microparticles in microfluidic systems"); U.S. Pat. No. 6,503,504 ("Delivery of bioactive compounds to an organism"); U.S. Pat. No. 6,411,842 ("Implant device for internal-external electromyographic recording, particularly for the in vivo study of electromotor activity of the digestive system"); U.S. Pat. No. 6,285,897 ("Remote physiological monitoring system"); U.S. Pat. No. 6,403,647 ("Pulsed administration of compositions for the treatment of blood disorders"); U.S. Pat. No. 6,360,123 ("Apparatus and method for determining a mechanical property of an organ or body cavity by impedance determination"); U.S. Pat. No. 6,329,153 ("Method for evaluating immunosuppressive regimens"); U.S. Pat. No. 5,985,129 ("Method for increasing the service life of an implantable sensor"); U.S. Pat. No. 5,779,631 ("Spectrophotometer for measuring the metabolic condition of a subject"); U.S. Pat. No. 5,569,186 ("Closed loop infusion pump system with removable glucose sensor"). Those skilled in the art will also recognize how to apply numerous existing techniques for taking provisional, alternate, overlapping, or completion actions relating to such applications as exemplified herein without undue experimentation, in light of these teachings. Sense module 822 may be configured to transmit one or more selection indications wirelessly, for example, or to communicate such information via a signal conduit to module 810, which subsequently transmits an audible or other wireless signal. In some variants, for example, module 810 includes a signal bearing conduit to a speaker in a subject's jaw or ear to notify the subject of a dispensation.

An enlarged view is shown of a portion of tether 837 comprising a segment 841 having one or more flow path(s) 838 for a fluid material to be released into digestive fluid 865 through dispenser 821 (when valve 820 is open). Valve 820 may actuate as a mechanical response to the fluid material exceeding a threshold pressure and/or as an electromechanical or other response to other information passing through the flow path(s) 838. Tether 837 may likewise include segment 842 to other dispensers and/or sense modules, optionally coupled via extensions of one or more of the flow paths 838 as shown. Segment 842 may optionally comprise optical fiber, for example, providing mechanical support for and an image data flow path from one or more lenses or other sensors.

Figure 9:
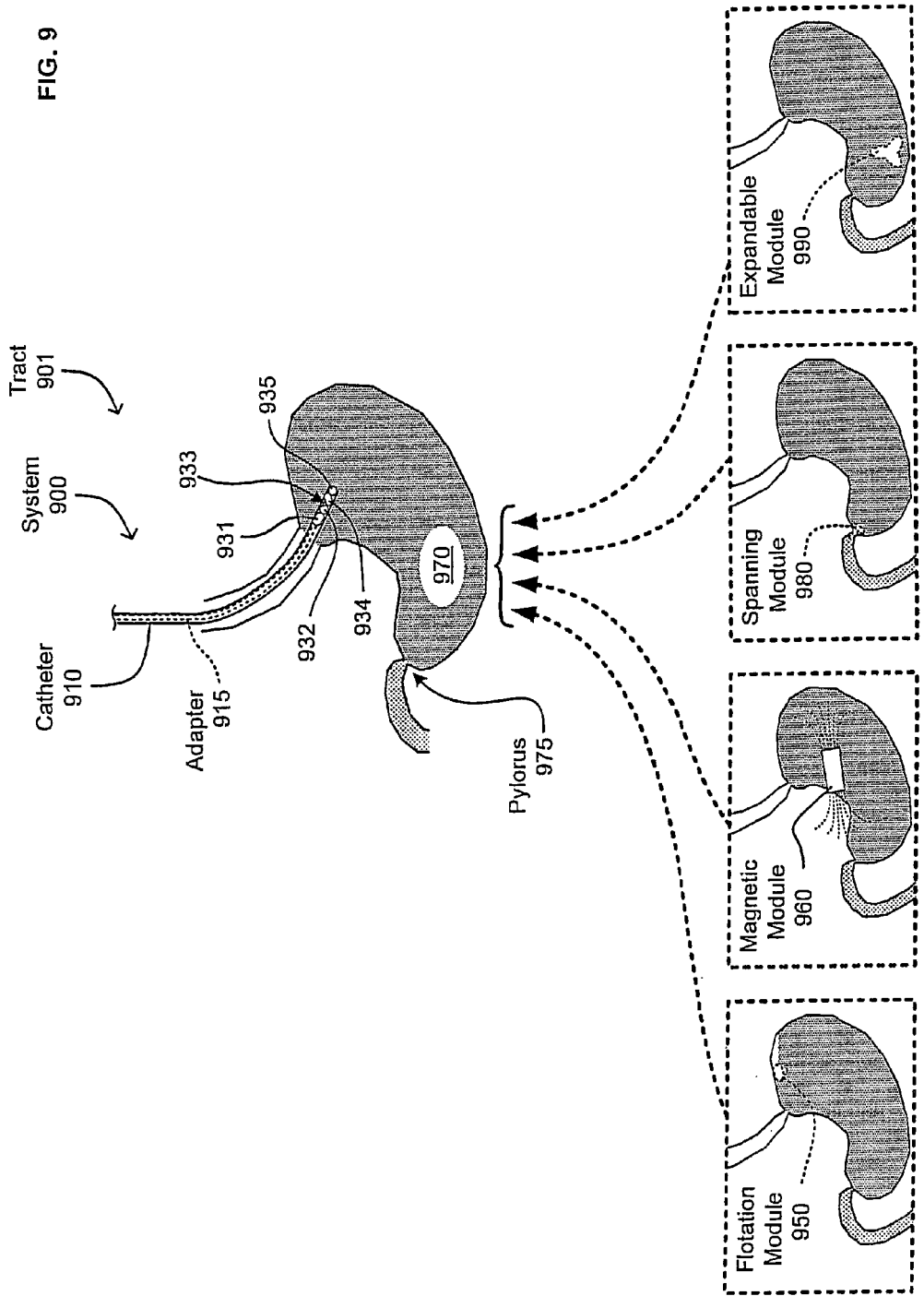

With reference now to FIG. 9, shown is an example of a system that may serve as a context for introducing one or more processes and/or devices described herein. As shown system 900 may (optionally) include a catheter 910 containing several modules 931, 932, 934, 935 each within gastric compartment 970 and small enough to pass through tract 901 individually. In some variants, catheter 910 may be small enough to pass through a nasal passage, for example. Alternatively or additionally, catheter 910 may comprise one or more inner sleeves or other adapters 915 configured for use in manipulating one or more modules in situ, such as by urging module 931 outward, by applying an adhesive, by cutting a tether, or for other operations as described herein in various implementations. As shown, most or all of such modules 931, 932, 934, 935 are strung onto a common tether 933, preferably in a configuration that is dosed, sequenced, or otherwise tailored for administration to a specific patient, and optionally within a soluble capsule. In some variants, the tether is strung through a non-axial portion of one or more intermediate modules 932, 934 so that tension in the tether tends to urge the grouping of modules to become less coaxial. Such tension can be preloaded in an elastic length of tether 933, for example, so that a shape change occurs immediately in response to an expulsion from catheter 910 or a capsule, or later in response to detectable environmental changes. Such shape changes may be configured to occur in response a sufficiently-long exposure to an acidic and/or aqueous environment, a body-temperature environment, an electrically conductive environment, or other such environmental circumstances indicative of entry into a specific portion of a digestive tract of a given subject. Such shape changes in gastric compartment 970 may cause a grouping of several modules 931, 932, 934, 935 to become too large to pass through pylorus 975 and too irregular for them to become a problematic blockage. For example, some or all of the modules 931, 932, 934, 935 may be configured to swell or otherwise remove slack from and/or introduce tension into tether 933. If tether 933 is configured in a loop, for example, such swelling will tend to cause the modules to become less collinear, and thus less likely for pylorus 975 to be blocked.

In most contexts, a single module is "small enough to pass through a digestive tract" if a physician, veterinarian, or other skilled care provider would consider it safe for an inert item of that size to pass through the tract without becoming an obstruction. For most human beings and other mammals this corresponds with a module that is narrower than an eyeball (e.g., at most about 2 centimeters wide) and at most a few times as long as the eyeball (e.g., up to several centimeters long), and a slightly larger size for highly pliable modules. An unobstructed, normal digestive tract in a human adult of typical size, for example, may reasonably be expected to pass an inert module as large as a penny or AAA battery but not one as large as a typical pen or golf ball.

In most contexts, a module may be described as "at least 10% as large" as an item if the module is at least 10% as long as the item. The module is likewise "at least 10% as large" as the item if the module is at least 10% as voluminous as the item, taking the volume of each to include the volume of any bores or other regions of concavity therein. In an embodiment in which module 932 is "at least 10% as large" as module 931, for example, either of these module may accordingly be larger than the other in terms of length or volume.

In most contexts, a tether is "operable for coupling" modules via a gap if the tether helps to maintain the modules in a vicinity of each other by extending at least partly into the gap.

One or more such tethers may wrap around several such modules, for example, securing them at least partly within one or more recesses of a ring, spool, or cup.

In some variants, system 900 is initially configured so that catheter 910 contains several modules 931, 932, 934, 935 each small enough to pass (safely) through digestive tract 901. As shown, "second" module 935 may be sized within an order of magnitude of "first" module 931, at least in terms of length, and/or with "second" module 935 somewhat shorter than "first" module 931. Alternatively or additionally, "third" module 934 may (optionally) be at least half as voluminous as "first" and/or "second" modules 931, 935. One or more instances of intermediate modules 932, 934 may (optionally) each comprise a unitary body having an overall average density smaller than 0.9 grams per milliliter, such modules tending to remain in gastric compartment 970 for a time even after tether 933 no longer operates.

Various modes of surgery-optional and/or catheter-optional deployment are described herein for maintaining mooring and/or utility modules in a gastric compartment for a controllable and/or extended period—4 hours, a day, a week, a month, or more—in various contexts. Such prolonged durations may be achieved, for example, by including one or more flotation modules 950, one or more magnetic modules 960, one or more (pylorus-)spanning modules 980, one or more expandable modules 990, suitable adhesion or piercing features, or other modes as described herein. For example, various configurations of magnetic-flux-generating or other magnetic-flux-guiding modules may be implanted or otherwise positioned adjacent pylorus 975, on a removable belt worn by a subject, or otherwise in a vicinity of digestive tract 901.

Figure 10:
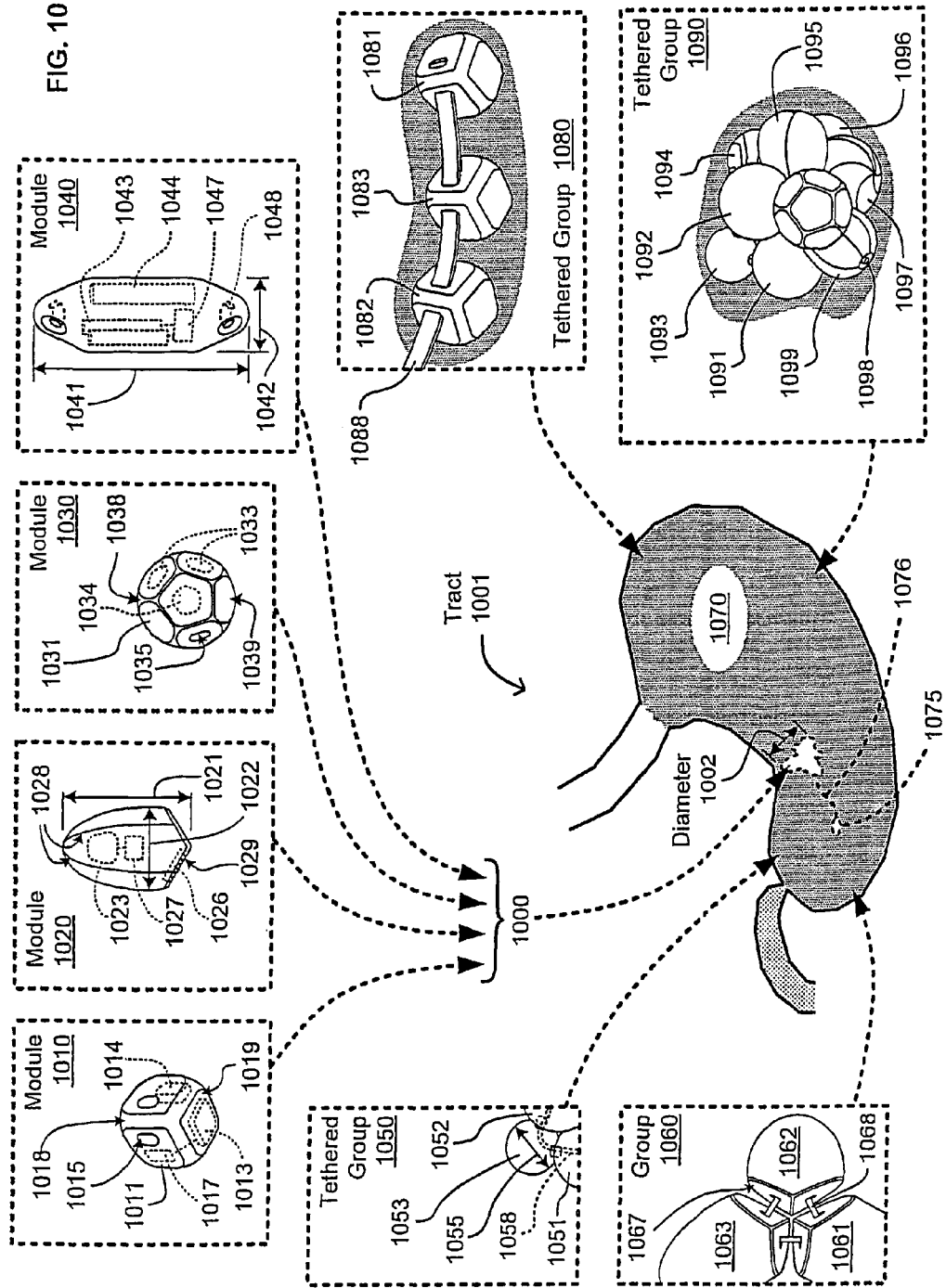

With reference now to FIG. 10, shown is an example of a system that may serve as a context for introducing one or more processes and/or devices described herein. As shown digestive tract 1001 may include gastric compartment 1070 containing one or more systems 1000 such as tethered groups 1050, 1060, 1080, 1090. Each such system 1000 may include one or more instances of modules 1010, 1020, 1030, 1040 as shown, for example, in a sufficient number so that system 1000 has an effective cross-sectional diameter 1002 too large to permit exit from gastric compartment 1070 in any orientation. Some embodiments of system 1000 may further comprise one or more additional modules 1075 coupled with such a group by surgical thread or a similarly flexible tether 1076 about 1 centimeter or more in length.

System 1000 may include one or more modules 1010 each comprising a cube-like unitary body 1011 with six primary external surfaces 1019 all bounded by a substantially convex external surface 1018. Module 1010 may further include one or more instances of bores 1015 or other gaps configured to facilitate passage or other guidance of one or more tethers as described herein. Module 1010 may also include one or more instances of (incremental) dispensers 1013, 1014, fluidic access to at least some of which may be controlled by circuitry 1017 as described herein.

Alternatively or additionally, system 1000 may (optionally) include one or more modules 1020, an instance of which is shown at a somewhat magnified scale similar to that of module 1010. Module 1020 may comprise an oblong unitary body having a length 1021 of about 1 millimeter or larger, and at least 10% greater than its cross-sectional diameter 1022. The body is bounded by an upper surface having (at least somewhat) longitudinal ribs 1028 as well as a plurality of other faces 1029. At least one such face 1029 may be situated adjacent one or more flux-guiding elements 1026 operable for responding to a magnetic field within a portion of the digestive tract. Such an instance may thus tend to align (or resist misalignment) with one or more other modules of system 1000, for example, if either is implemented as a permanent magnet or electromagnet. This can be particularly useful for controlling a mode of expansion in embodiments like that of group 1060 in which opposite ends of the tether are situated in different modules, for example. While in the digestive tract, moreover, such flux-guiding elements may be safely and reliably drawn to a tract wall, for example, by providing a strong magnetic field from outside the digestive tract. Module 1020 may likewise include one or more instances of dispensers 1023, fluidic access to at least some of which may be controlled by circuitry 1027 as described herein.

Alternatively or additionally, system 1000 may (optionally) include one or more modules 1030, an instance of which is shown at a somewhat magnified scale similar to those of other modules 1010, 1020 described above. Module 1030 as shown has a unitary, substantially polyhedral body 1031 with one or more convex external surfaces 1038 and several other surfaces 1039. (In some embodiments, such other surfaces 1039 may each comprise saddle regions, recesses, or otherwise structured surfaces as described herein.) Module 1030 may include one or more instances of passive dispensers 1033 each containing 1-15 grams of medicinal material configured to dissolve somewhat uniformly in gastric compartment 1070 over one or more days, weeks, or months. Module 1030 may likewise include one or more instances of dispensers 1033, 1034 and/or rotationally asymmetric gaps 1035 for accommodating various tether configurations as described herein.

Alternatively or additionally, system 1000 may (optionally) include one or more modules 1040, an instance of which is shown at a somewhat magnified scale similar to those of other modules 1010, 1020, 1030 described above. Module 1040 may (optionally) comprise a unitary body having an overall average density smaller than 0.9 grams per milliliter and/or a cross-sectional diameter 1042 larger than one millimeter. Alternatively or additionally, module 1040 may include one or more passages 1048 or other gaps collectively sufficient for receiving more than one tether or tether winding. Module 1040 may likewise include one or more instances of dispensers 1043, 1044, fluidic access to at least some of which may be controlled by circuitry 1047 as described herein.

In some embodiments, system 1000 may be configured so that the "first" module comprises module 1010, so that the "second" module comprises module 1020, and so that the "third" module comprises module 1030, all coupled by a single common tether. In some such embodiments, the relative scaling of modules 1010, 1020, 1030 is such that "second" module 1020 (i.e. at length 1021) is at least half as long and/or voluminous as "first" module 1010. Alternatively or additionally, "third" module 1030 may (optionally) be made larger so that it is more voluminous than "first" module 1010 and/or "second" module 1020. In some variants, moreover, system 1000 may further comprise one or more instances of module 1040 as shown, a "fourth" module having a length 1041 more than twice the width thereof. Alternatively or additionally, tract 1001 may (optionally) contain tethered group 1050 comprising several modules 1051, 1052, 1053 bound together by a single common tether 1058. Tethered group 1050 may likewise include other modules, some or all of which may optionally be bound by other tethers (not shown) to create a desired configuration. In some embodiments, module 1053 may have a cross-sectional diameter 1055 larger than one millimeter, optionally 2-5 millimeters or larger.

Alternatively or additionally, tract 1001 may (optionally) contain group 1060 comprising several modules 1061, 1062,

1063 bound together by a single, primarily elastic tether 1068. (Group 1060 is shown in tension to expose a plurality of substantially flat faces 1067 on each module.) In some embodiments, group 1060 is configured so that the "first" module comprises module 1061 and so that the "third" module comprises module 1063, and so that one or both of these implement module 1020. Module 1061 may (optionally) comprise one or more instances of dispenser 1023 containing a total of 1-15 grams of medicinal material, for example, such as an antibiotic or statin. Moreover in some variants "third" module 1063 may be more than half as voluminous as, or may be more voluminous than, "first" module 1061 and/or "second" module 1062. Alternatively or additionally, "third" module 1063 may be at least half as long as, or may be longer than, "first" module 1061 and/or "second" module 1062.

Alternatively or additionally, tract 1001 may (optionally) contain tethered group 1080 comprising several modules 1081, 1082, 1083 (each small enough to pass through tract 1001 individually but prevented from such passage by virtue of being) bound together by a single common tether 1088. Any or all of modules 1081, 1082, 1083 may be configured as instances of module 1010, each optionally implementing circuitry 1017, dispenser 1013, or other attributes of module 1010 as described herein. As shown, modules 1081-1083 may be supported along at least a rotationally asymmetric portion of tether 1088. Alternatively or additionally, the "third" module 1083 may be at least half as voluminous as the "second" module 1082.

Alternatively or additionally, tract 1001 may (optionally) contain tethered group 1090 comprising several modules 1091, 1092, 1093, 1094, 1095, 1096, 1097, 1099, at least some of which are small enough to pass through tract 1001 individually but prevented from such passage by virtue of being bound together in tethered group 1090. Any or all of modules 1091-1097 and 1099 may be configured as instances of other modules described herein. Tether 1098 binds together at least a "first" module 1099 and some of the other modules 1091-1097. Alternatively or additionally, as shown, "first" and/or "second" ones of modules 1094-1097 may each be more than twice as long as each respective width thereof.

Figure 11:
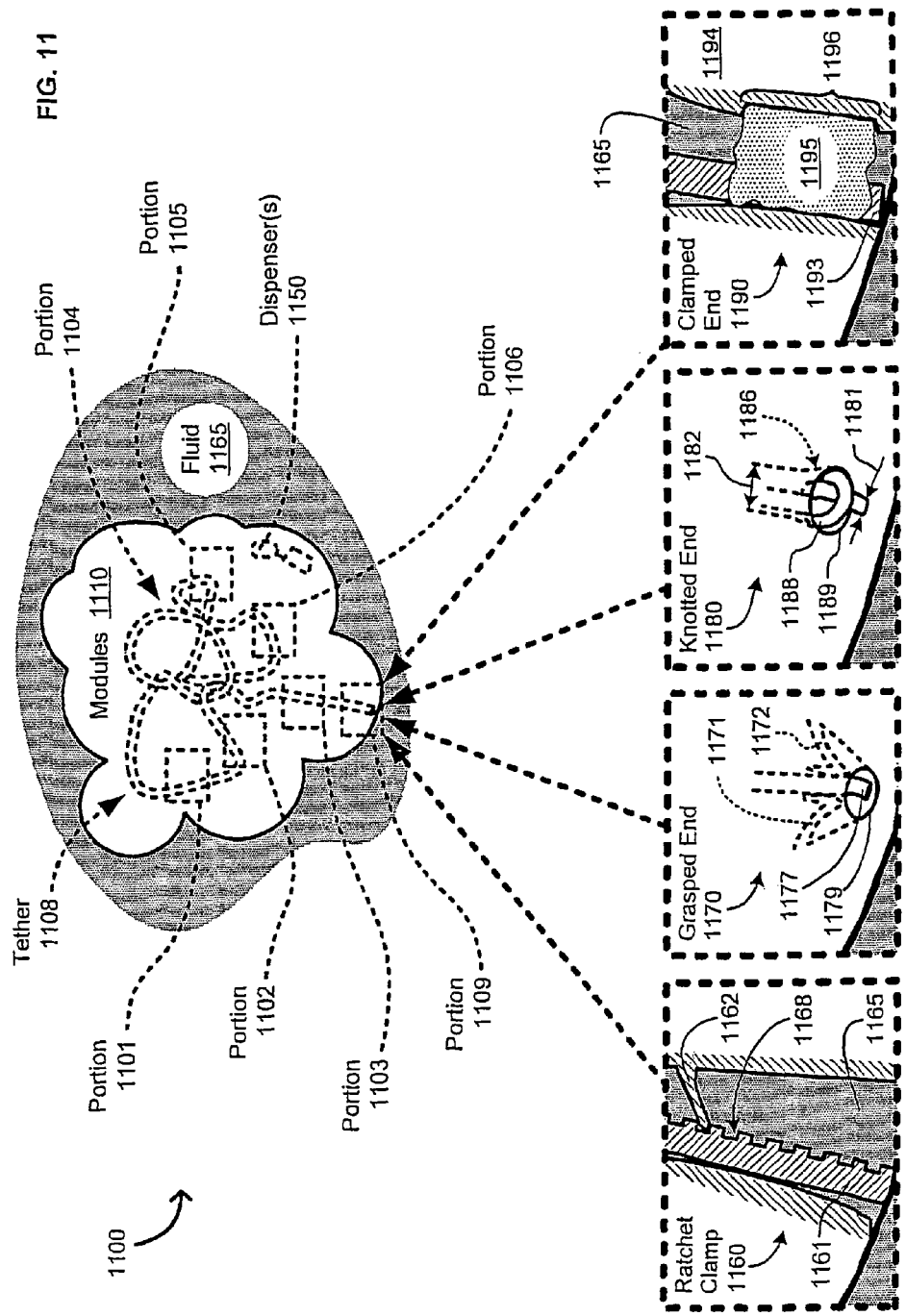

With reference now to FIG. 11, shown is an example of a system that may serve as a context for introducing one or more processes and/or devices described herein. As shown system 1100 may include at least one tether 1108 binding several non-aligned modules 1110 within fluid 1165. Tether 1108 may comprise one or more distal portions 1109 bounding a "middle" portion 1104 containing or otherwise overlapping one or more other portions 1101, 1102, 1103, 1105, 1106. Each of modules 1110 is roughly of similar size and small enough to pass through an entire digestive tract containing fluid 1165 (at least after an appropriate deflation). Tether 1108 effectively couples a "first" and "second" ones of modules 1110 via a gap in (at least) a "third" module, tether 1108 having at least a middle portion 1104 configured to slip free from the "third" module responsive to the tether breaking or being released.

In some embodiments, any "first" or "second" module as described herein may comprise a ratchet clamp 1160 comprising one or more flexible members 1162 extending into one or more corresponding recesses 1168 of tether 1161 so that tether 1161 can be pulled outward (downward as shown) from the module but resists retraction. In some variants of system 900 (of FIG. 9), for example, such a mechanism can be used by adapter 915 to remove slack from (and optionally place static tension into) at least a middle portion of tether 933. Excess length of tether 933 can then be pulled free (if notched or perforated, for example) or cut off (with a cutting device of adapter 915, for example, not shown).

Alternatively or additionally, any "first" or "second" module as described herein may comprise a grasped (tether) end 1170 comprising one or more flexible members 1171, 1172 gripping a rotationally symmetric portion of an end of tether 1177 at an orifice 1179 (such as may implement distal portion 1109 of tether 1108). In some variants, such flexible members 1171 may be calibrated so that they will release tether 1177 in response to a predetermined tensile force (upward as shown) urging tether 1177 to be released by the module. In some variants, a tether 1177 includes a smooth distal portion 1109, facilitating the release of such modules from the "second" module, for example.

Alternatively or additionally, any "second" or "third" module as described herein may comprise a knotted (tether) end 1180 in which a stopper or other suitable knot 1188 is used in conjunction with a bore 1189 having a cross-sectional diameter 1182 larger than a cross-sectional diameter 1181 of the tether but smaller than that of the knot 1188. The bore may (optionally) have a tapered portion 1186 so that part of the bore is large enough to accommodate a portion of the knot.

Alternatively or additionally, any module as described herein may comprise a clamped end 1190 in which an adhesive and/or expansive element 1195 expands or otherwise emerges when exposed to fluid 1165 (from one or more recessed portions 1196 of module 1194, for example) to secure a distal portion of a tether 1193. Such clamping may result from adhesive activation and/or from a compression fit, for example, resulting from element 1195 reacting to water in fluid 1165.

In some embodiments, system 1100 comprises several ("first," "second," and "other") modules 1110 bound by tether 1108, optionally for deployment via a flexible catheter or soft gelatin capsule into an animal needing treatments over an extended period (of several days or months, for example). Any or all such modules 1110 may each comprise one or more instances of circuitry for controlling one or more dispensers 1150 and/or a unitary body having an overall average density smaller than 0.9 grams per milliliter. In some embodiments, for example, enough buoyant modules may be included so that the overall average density of system 1100 is smaller than that of fluid 1165.

In some embodiments, a therapeutic agent may be placed into one or more dispensers 1150 described herein, optionally packaged with one or more solid or gel phase carriers or excipients. Examples of such carriers or excipients include, but are not limited to, croscarmellose sodium, povidone, microcrystalline cellulose, calcium carbonate, calcium phosphate, various sugars, starches, cellulose derivatives, pregelatinized starch, polymers such as polyethylene glycols, lactose, lactose monohydrate, sucrose, talc, gelatin, agar, pectin, acacia, magnesium stearate, stearic acid and substantially any combination thereof.

In some embodiments, therapeutic agents that are hydrophobic may be packaged through use of a cosolvent system comprising benzyl alcohol, a nonpolar surfactant, a water-miscible organic polymer, and an aqueous phase. The cosolvent system may be the VPD co-solvent system. VPD is a solution of 3 percent weight/volume benzyl alcohol, 8 percent weight/volume of the nonpolar surfactant polysorbate 80, and 65 percent weight/volumen polyethylene glycol 300, made up to volume in absolute ethanol. The VPD co-solvent system (VPD:5W) consists of VPD diluted 1:1 with a 5 percent dextrose in water solution. This co-solvent system dissolves hydrophobic therapeutic agents well, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol (i.e., polyvinyl pyrrolidone; and other sugars or polysaccharides may substitute for dextrose). Many other delivery systems may be used to administer hydrophobic therapeutic agents as well. For example, liposomes and emulsions are well known examples of delivery vehicles or carriers for hydrophobic drugs. Certain organic solvents such as dimethysulfoxide also may be employed, although usually at the cost of greater toxicity.

Some therapeutic agents may be packaged as salts with pharmaceutically compatible counter ions. Pharmaceutically compatible salts may be formed with many acids, including hydrochloric, sulfuric, acetic, lactic, tartaric, malic, succinic, etc. Salts of therapeutic agents tend to be more soluble in aqueous or other protonic solvents than are the corresponding free-base forms.

Numerous carriers and excipients are known and are commercially available (i.e., The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, PDR, Montvale, N.J. 2004; U.S. Pat. Nos. 6,773,721; 7,053,107; 7,049,312 and Published U.S. Patent Application No. 20040224916; herein incorporated by reference to the extent not inconsistent herewith). In some embodiments, such methods may be used with regard to one or more dietary or other regimen compliance objectives and/or combinations of one or more pharmaceutical or nutraceutical agents with one or more aspects of diet, or other subject attributes.

One or more instances of tethers 1108 among modules 1110 may (optionally) include one or more elastic (length) portions 1101 each operable for a nominally elastic deformation of at least 10%. (Middle portion 1104 contains or otherwise at least overlaps elastic portion 1101.) In some variants system 1100 is configured with one or more such elastic portions 1101 totaling at least half of (an entire length of) tether 1108. Alternatively or additionally, tethers described herein may comprise one or more inelastic portions 1102 (of middle portion 1104) optionally including a notch or other configured breakage mechanism. In some contexts, nominally "inelastic" length portions normally deform permanently or break if stretched by 10% or more.

In some embodiments, a "semi-soluble" element is one that is configured to break down in more than an hour but less than a week, and a "substantially insoluble" element is less soluble than this. Numerous water insoluble polymers may be used to reduce a compound's solubility, for example, such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such less-soluble elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 3 to 30 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release of one or more therapeutic agents that are wrapped in such a wrapper following administration to an individual.

In some embodiments, one or more therapeutic agents may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048, 945; 7,056,951; hereby incorporated by reference to the extent not inconsistent herewith).

In some embodiments, tethers described herein may be made integrally with one or more modules and/or include one or more strands of surgical thread, polymer, or other materials of suitable elasticity and strand structure. In many contexts, tether 1108 may be implemented to include one or more other instances of soluble portions 1105, dispensers 1150 or inelastic portions 1106 (of middle portion 1104). In some variants, for example, inelastic portion 1106 may be configured to separate when loaded with more than a calibrated tension T, where T is at least 1-10 pounds and/or at most 10-100 pounds. Tether 1108 may, for example, be configured as a compound structure that includes one or more modules joining two or more tether segments end-to-end. Tether 1068 may likewise be formed as a loop, for example, by module 1061 grasping both ends of a simple tether passing through other modules 1062, 1063.

Figure 12:
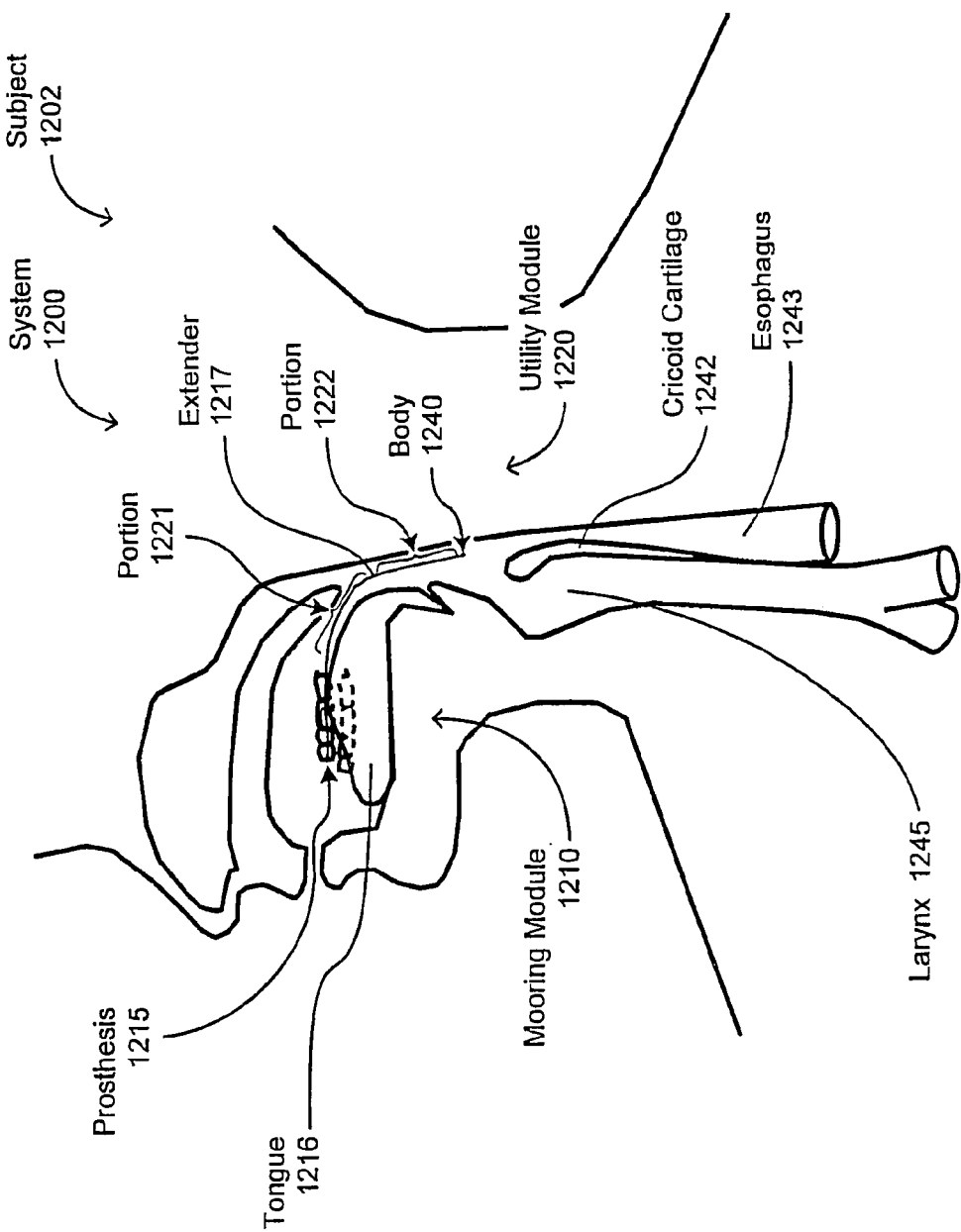

With reference now to FIG. 12, shown is a system positioned at least in a vicinity subject 1202 in which one or more technologies may be implemented. System 1200 may comprise one or more medical or veterinary utility modules 1220 comprising one or more bodies 1240 supported via one or more adaptable extender modules comprising a (rigid or other) prostheses 1215 or other support within the head and/or neck position and one or more supple extenders 1217 therefrom. Alternatively or additionally, such extenders or their portions 1221, 1222 may likewise be supported nasal stents, surgical staples in cranial or throat positions (such as the hard palate, nasal cartilage, or cricoid cartilage 1242, for example), nasal stents, or other such mooring modules 1210. Exemplary structures and modes of operation may be found, for example, in U.S. patent application Ser. No. 11/417,898 ("Controllable release nasal system"), having overlapping inventors herewith, incorporated by reference herein. See also U.S. patent application Ser. No. 11/716,645 ("Orthonostric device and method of forming the same"). In some variants, extender 1217 may pass beside tongue 1216 and optionally into a side of the throat of subject 1202 with minimal interaction with the soft palate. Alternatively or additionally, a tether or other portions 1221, 1222 of one or more extenders 1217 may be coated along at least some of their length with an anesthetic-containing material.

Such tethers or other such supple structures may extend into esophagus 1243 or other parts of subject 1202, as described farther below. Body 1240 may comprise one or more auditory or other sensors as described herein. Body 1240 may likewise comprise one or more dispensers, particularly those having a flow path from reservoir positions at oral and/or gastric modules 141, 144 (as shown in FIG. 1). In some variants, an upper portion 1221 of extender 1217 has a flexural modulus of at least about 10 megapascals. Alternatively or additionally, a lower portion 1222 has a flexural modulus of at most about 20 megapascals. Such extenders may likewise include one or more active components (not shown) operable to bend one or more coupling to keep mucous membrane irritation at an acceptably low level.

Figure 13:
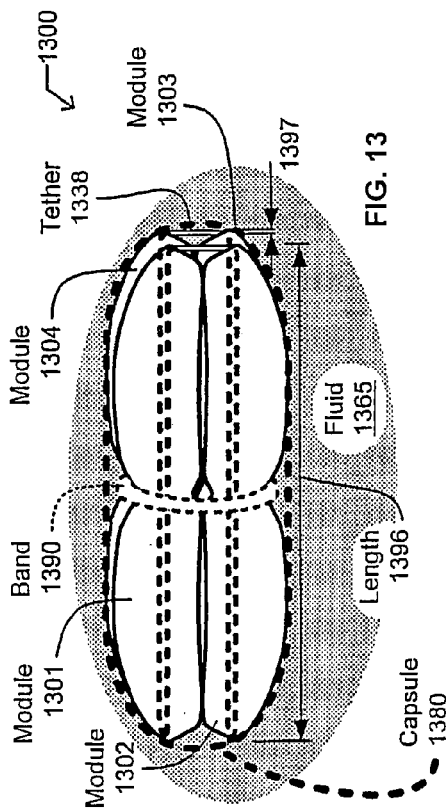

With reference now to FIG. 13, shown is an example of a system 1300 immersed in digestive fluid 1365. System 1300 comprises several modules 1301, 1302, 1303, 1304 strung onto a single common tether 1338 having an average diameter 1397 less than 10% of length 1396. The modules 1301-1304 may be held together by one or more capsules 1380 and/or bands 1390 to facilitate ingestion. As shown, system 1300 may (optionally) include one or more longest modules 1303, 1304 having a length 1396 about 1-2 times that of an eyeball of the subject). For a typical human adult, for example, such a length 1396 may be longer than 3 centimeters and/or less than 6 centimeters.

Figure 14:
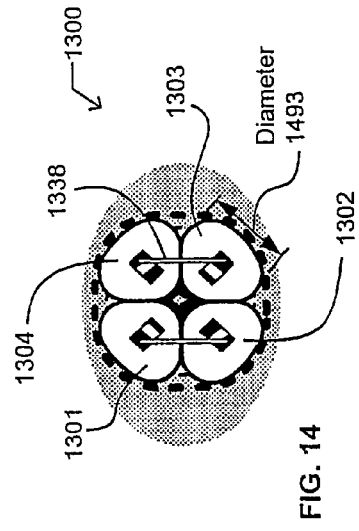

With reference now to FIG. 14, shown is an end view of system 1300 (as viewed from the right, relative to FIG. 13). Each of modules 1301-1304 has roughly the same diameter 1493 as one another, as shown, within a factor of 2. Alternatively or additionally, one or more of modules 1301-1304 may likewise have roughly the same length as length 1396, within a factor of 2.

Figure 15:
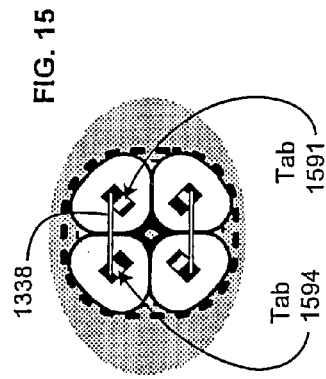

With reference now to FIG. 15, shown is an end view of system 1300 (as viewed from the left, relative to FIG. 13). Unlike the view in FIG. 14, tether 1338 appears roughly horizontal, stretched between respective tabs 1591, 1594. Each of modules 1301-1304 has one or more tabs 1591, 1594 at each end as shown.

Figure 16:
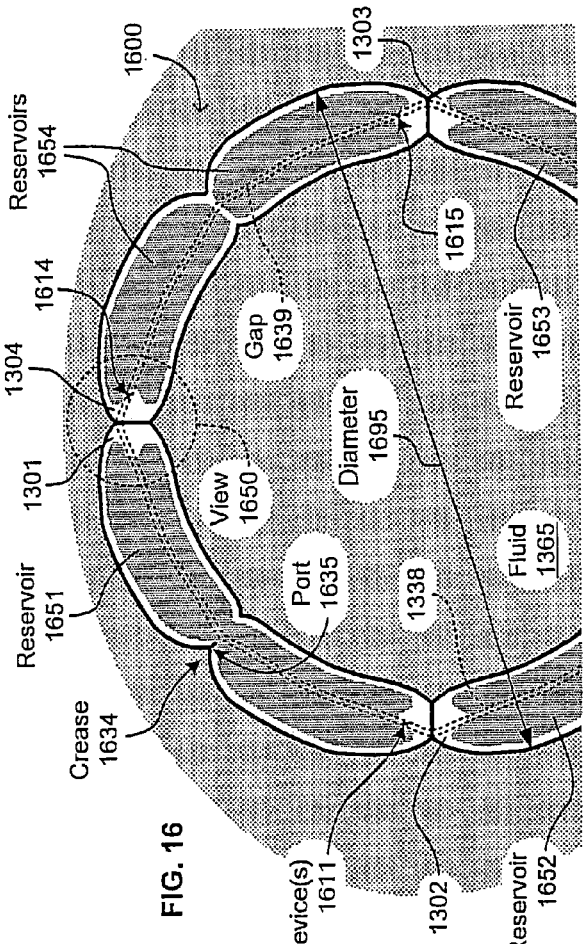

With reference now to FIG. 16, shown is an example of a medical or veterinary system 1600 comprising the modules 1301-1304 of FIGS. 13-15 in a fully expanded configuration. Tether 1338 may be configured as a taut loop in this configuration, effectively coupling each pair of these modules 1301-1304 via a bore or other gap 1639 in each of the modules. In a variant in which one or more device(s) 1611, 1615 is configured to sever or otherwise release respective ends of tether 1338 within gap 1639 of module 1301, for example, the gaps 1639 of one or more other modules 1302-1304 are large enough to permit tether 1338 to slip free so that all of the modules 1301-1304 may pass separately and safely per vias naturales. Such device(s) 1611, 1615 may (optionally) be configured to effect such a release in response to one or more of a temperature change indicating entry into a stomach, a pH change of more than 2 points or some other indication of a sensed position, a remote control signal, an excessive tension in tether 1338, or some other indication that system 1600 should or should not be fully expanded in a subject's current circumstances. Such device(s) 1611 may be configured to permit a clinical care provider to prevent or abort a deployment in the event that system 1600 has apparently begun to deploy in an esophagus or small intestine, for example. In some variants, such a ring-type module may support a tube or other tether extending out of a gastric compartment as described herein.

For a typical human adult, a deployed diameter 1695 may (optionally) be longer than 4 centimeters and/or less than 8 centimeters. As shown, modules 1301-1304 each has a nominal module length more than twice as long as its (respective) average cross-sectional diameter 1493. At least one of the modules 1303 may (optionally) have exactly one reservoir 1653. In some variants, each such reservoir 1652, 1653 may contain a respective therapeutic agent or a partial dosage of a common therapeutic agent. Alternatively or additionally, each such reservoir 1652, 1653 may be configured for dispensation under respectively different conditions. In some variants, for example, one or more other reservoirs 1651, 1654 may comprise a dispenser containing one or more of an antiviral or other antimicrobial agent, or some other component of a complex therapeutic regimen. In some variants, one or more such reservoirs 1651-1654 may comprise one or more of an anti-seizure medication, warfarin or other anticoagulant medications, insulin or other hormones, or other dosage-sensitive therapeutic agents.

To achieve the expanded configuration of system 1600 conveniently, at least some of tether 1338 may (optionally) be constructed of a sufficiently elastic material able to be stretched by at least about 5-10% with negligible damage. Alternatively or additionally, some or all of tether 1338 may be constructed to contract in an aqueous and/or acidic environment. Alternatively or additionally, one or more modules 1301-1304 may advantageously comprise an initially compressed body (especially as shown in FIG. 13), a body that swells in an aqueous and/or acidic environment, a shape memory element, and/or some other suitable uptake mechanism. Many such existing uptake mechanisms may be effectively implemented for this purpose (in device 1614, for example) without undue experimentation, as exemplified at FIG. 7 of U.S. patent application Ser. No. 11/975,371, titled "Disintegrating Digestive Tract Interaction System," filed 17 Oct. 2007, issued as U.S. Pat. No. 8,038,659, also by Boyden et al. Such an active uptake mechanism may be triggered by a disengagement of band 1390, a significant increase of ambient conductivity (and/or pressure or temperature, e.g.), or some other deployment-indicative condition. Other changes can occur as a mechanical or automatic response to such changes, such as a relaxation in crease 1634 causing port 1635 to open.

Figure 17:
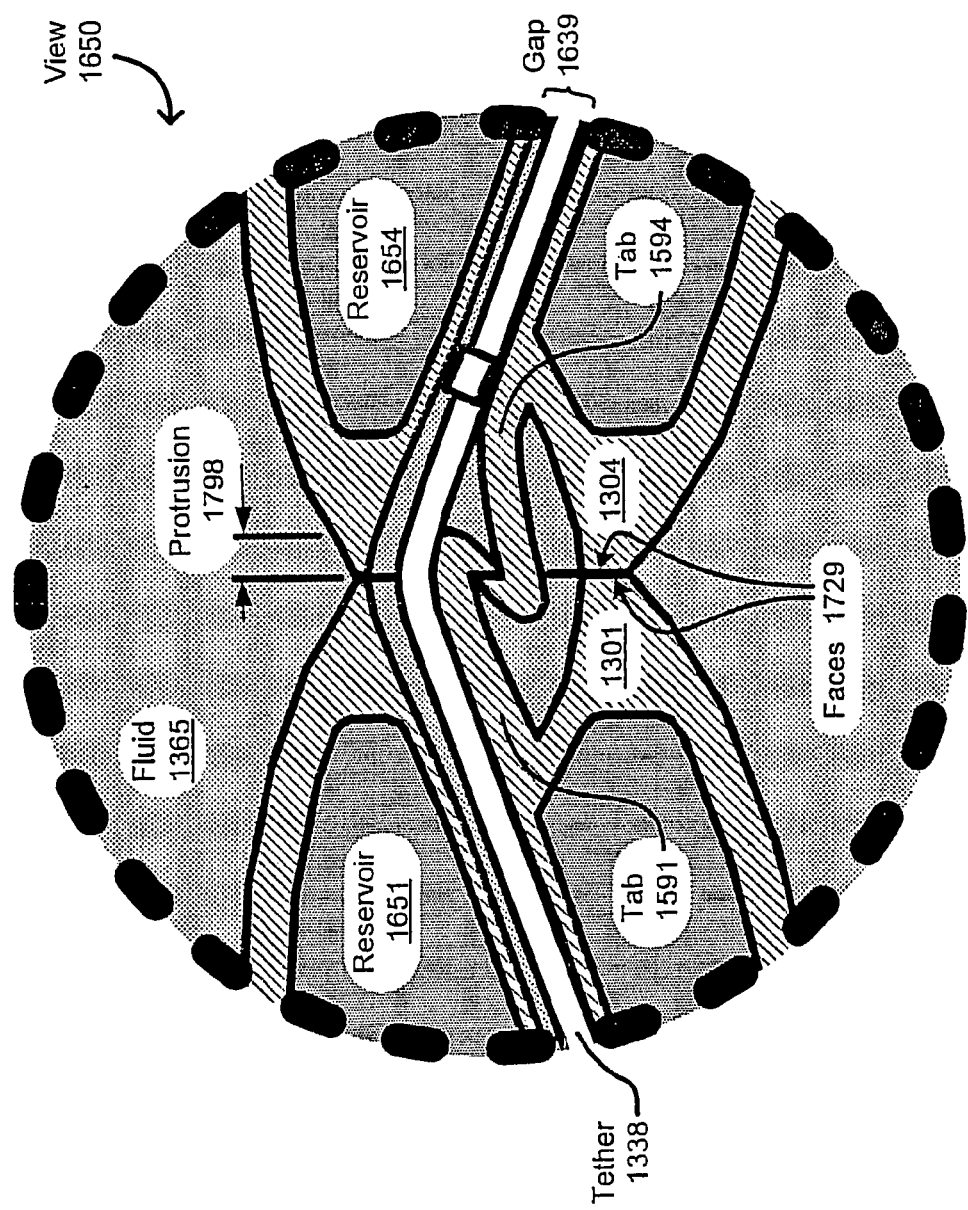

With reference now to FIG. 17, shown is a partial view 1650 of the expanded medical or veterinary system 1600 of FIG. 16, magnified and in cross-section. Here it is apparent that module 1301 comprises reservoir 1651 and a sleeve or other gap 1639 through which tether 1338 passes. Module 1304 likewise comprises reservoir 1654 and a sleeve or other gap 1639 through which tether 1338 also passes. Tether 1338 effectively couples module 1301 with module 1304 through gap 1639 as shown. Tether 1338 also has a "middle portion" (in FIG. 16) configured to slip free from modules 1302, 1303 responsive to tether 1338 dissolving, breaking, or otherwise decoupling module 1301 from module 1304.

To maintain an expanded configuration like system 1600 in a gastric compartment, in some variants, each adjacent pair of modules may advantageously include a magnetic, adhesive, mechanical, or other latching feature such as tabs 1591, 1594 operable to extend into an adjacent module, for example. Such tabs 1591, 1594 may latch together (as shown in FIG. 17) or otherwise engage as respective faces 1729 thereof are drawn adjacent one another by tension in tether 1338 (in response to immersion in fluid 1365, for example). The protrusion 1798 of tab 1591 into module 1304 may (optionally) be about one millimeter or less, as shown. In some variants, moreover, such an engagement mechanism may release or relax in response to a slackening of tether 1338. This can occur, for example, in a configuration in which tab 1591 bears (upward as shown) against tether 1338, optionally enough to release tab 1594 in response to an absence of force (downward as shown) exerted by tether 1338.

Figure 18:
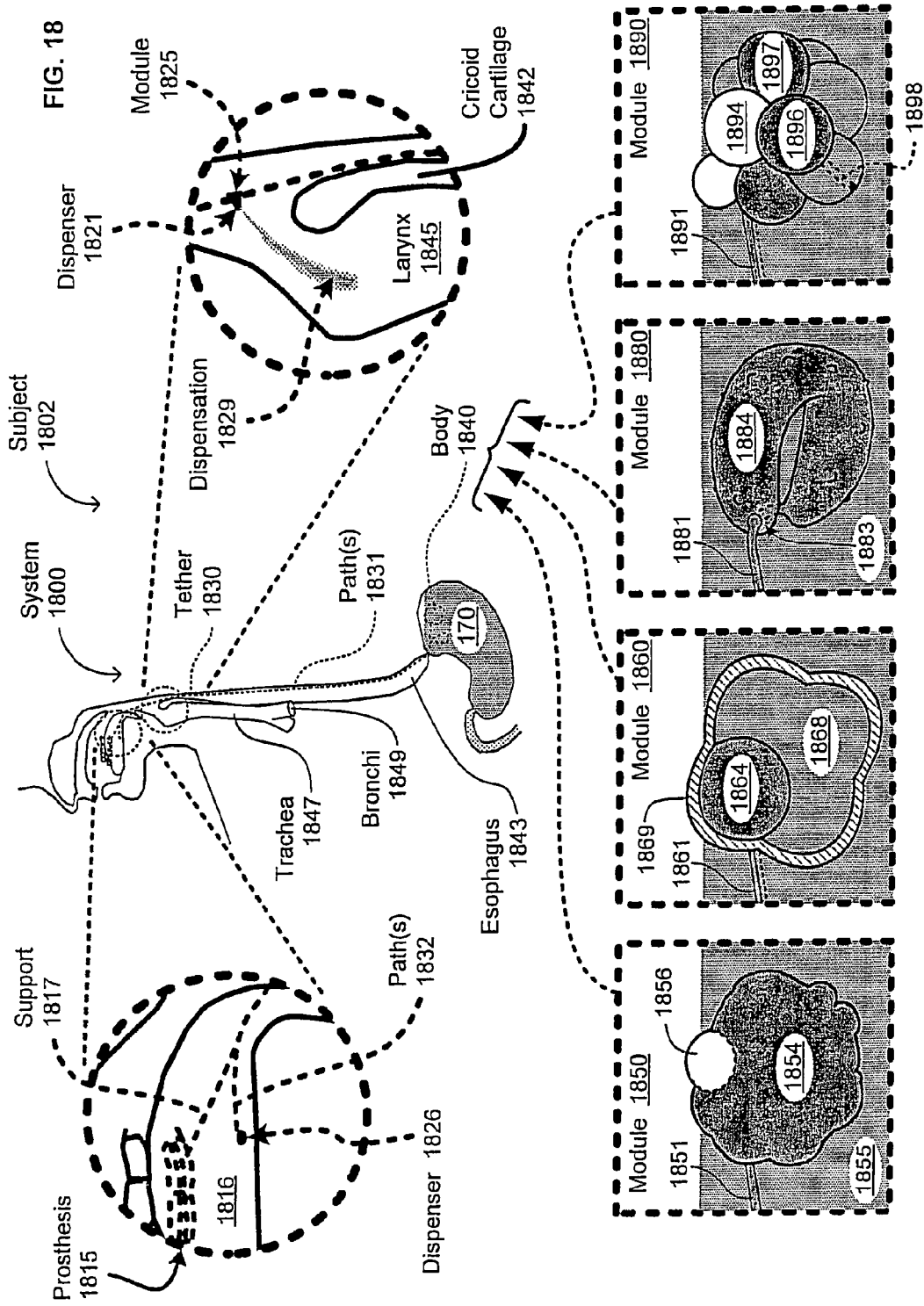

With reference now to FIG. 18, shown is a digestive tract portion and adjacent anatomical structures of a subject 1802 in a vicinity of which one or more technologies may be implemented. System 1800 may comprise one or more bodies 1840 respectively or collectively coupled with or via one or more tethers 1830 extending within or outside gastric compartment. In some variants, such tethers may extend downward (see FIG. 1) or upward into or through esophagus 1843. Tether 1830 may (optionally) extend to one or more dispensers 1821 and/or other modules 1825 in a vicinity of larynx 1845 or trachea 1847, for example, optionally permitting one or more therapeutic material dispensations 1829 (e.g. in pulmonary administrations via bronchi 1849). In various embodiments, such dispensations may comprise a mist, aerosol or other suspension, mixture, or other material combination as described herein. Such tethers may be supported by one or more dental prosthetheses 1815 via one or more supports 1817, or by simply being tied around a tooth. In some variants, support 1817 passes beside tongue 1816 and optionally into a side of the throat of subject 1802 with minimal interaction with the subject's soft palate. Alternatively or additionally, tether 1830 may be supported by being coated along its length with an anesthetic-infused adhesive, by being supported by a surgical staple or other implanted structure (e.g. at cricoid cartilage 1842), and/or by being fastened to one or more nasal stents or other such anatomical interface structures suitable for use in the present context. See, e.g., U.S. patent application Ser. No. 11/716,645 ("Orthonostric device and method of forming the same").

For insulin or other hormones, or hormone mimics, or for many other bioactive substances described herein, a formulation may be provided in a sufficiently concentrated form so that about 1 to 50 milligrams per day (or per dispensation) thereof is therapeutically effective. Such volumes are sufficient for treating a variety of pathologies according to existing inhaler regimens, for example, or for compliance with other physician-specified regimens, or for more appropriate responses to emergency situations. For a liquid formulation of this type, for example, dispenser 1821 may include a porous membrane through which a liquid formulation passes for aerosolization. A variety other suitable forms of dispenser 1821 are also readily implemented in light of teachings herein. See, e.g., U.S. Pat. No. 7,066,029 ("System and method for improved volume measurement"); U.S. Pat. No. 7,028,686 ("Inhaled insulin dosage control delivery enhanced by controlling total inhaled volume"); U.S. Pat. No. 6,889,690 ("Dry powder inhalers, related blister devices, and associated methods of dispensing dry powder substances and fabricating blister packages"); U.S. Pat. No. 6,655,379 ("Aerosolized active agent delivery").

In some variants, system 1800 may include one or more signal or other flow path(s) 1831 through or along tethers as described herein. One or more such paths 1831, 1832 may extend to a sublingual dispenser 1826, for example, or to or from a location in the throat, nasal passage, intestine 880 (of FIG. 8), or other site in a vicinity of tract 801 and/or subject 1802. In some variants, for example, a signal flow path responsive to a nutrient level detected at sense module 822 may (optionally) travel up tether 837 to one or more modules in gastric chamber 870 implementing one or more of modules 810, 850 comprising body 1840, for example. Such detectable nutrients may comprise one or more instances of proteins, fats, vitamins, minerals, trace elements, carbohydrates, or substantially any ratio or other combination thereof. Such detection may comprise a determination whether one or more measurements indicative of one or more such nutrients (or a determinant derived from them) are within a nominal range derived from empirical data, for example, or at a lower-than-nominal level or a non-ideal level.

Such signal flow may then undergo a programmatic aggregation or delay and/or change form (from optical or electrical to a pressure or other mechanical manifestation, for example) before triggering dispensation via one or more dispensers 821, 1821, 1826 optionally provided in systems 800, 1800 described herein. In some variants, moreover, such dispensation may be administered to other sites, such as by routing a small flow tube into a blood vessel or other location in the abdominal cavity through an incision in the esophagus.

In some variants, body 1840 may have an annular configuration of a general type exemplified in U.S. Pat. No. 4,758,436 ("Drug delivery device which may be retained in the stomach for a controlled period of time"). Alternatively or additionally, body 1840 may have attributes of one or more other instances of modules 1850, 1860, 1880, 1890 described next.

In an instance in which body 1840 includes one or more attributes of module 1850, for example, body 1840 may comprise a single reservoir 1854 and/or a single-reservoir port 1851 for dispensing one or more therapeutic materials as described herein. Module 1856 further comprises a bladder or other such lower-density internal structure so that module 1850 is at least somewhat buoyant relative to fluid 1855 as shown.

In an instance in which body 1840 includes one or more attributes of module 1860, for example, body 1840 may comprise a primary reservoir 1864 and one or more other reservoirs 1868 in respective chambers of a common container 1869, optionally having higher-than-ambient pressure (by at least 1%, for example, in absolute terms). In a variant in which primary reservoir 1864 contains one or more bioactive agents, reservoir 1868 may comprise a carrier, for example, or a pressure-maintaining reservoir. In some contexts it may be preferable that container 1869 itself have a density larger than 1.1 g/ml. This may permit reservoir 1868 to contain a gaseous component for example, even without bringing the overall density of module 1860 below 0.8 g/ml. Alternatively or additionally, module 1860 may adjoin one or more conduits or other ports 1861 configured for permitting a valve elsewhere to release bioactive substances therein.

In an instance in which body 1840 includes one or more attributes of module 1880, for example, body 1840 may comprise a reservoir 1884 with an irregular outer surface and/or one or more gaps 1883, actuators, or other features for facilitating a change in a configuration thereof in situ. To further understand the operation of such features, see, e.g., U.S. patent application Ser. No. 11/702,888 ("Gastro-intestinal device and method for treating addiction") or U.S. Pat. No. 6,994,095 ("Pyloric valve corking device and method"). By drawing tether 1881 through gap 1883 with a catheter or other manipulation device, for example, pressure one on or more fluids inside reservoir 1884 may be increased in situ.

In an instance in which body 1840 includes one or more attributes of module 1890, for example, body 1840 may comprise a plurality of reservoirs 1894, 1896 having respectively different therapeutic substances therein, one or more of which may be directly releasable through their openings 1898. Tether 1891 may likewise include flow paths in either direction (for inflating or dispensing from reservoir 1894, for example, or for bearing electrical signals in either or both directions). Module 1890 may, in particular, combine two or more respective features of reservoir-containing modules 1850, 1860, 1880 described above, in each of the (component) reservoirs 1894, 1896, 1897 shown. In some variants, moreover, one or more such reservoirs 1897 is configured for selective release as exemplified in relation to FIG. 19.

Figure 19:
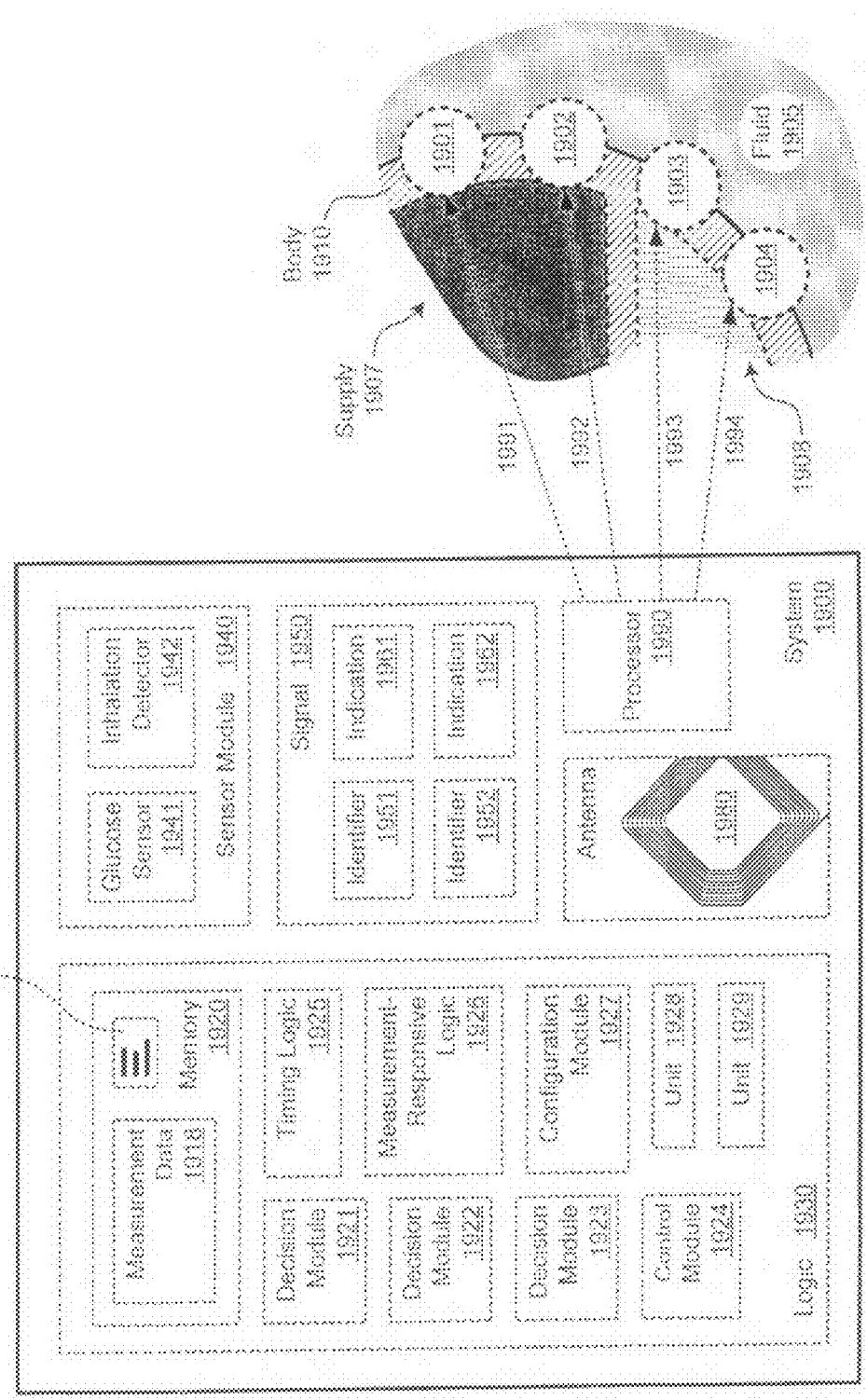

With reference now to FIG. 19, shown is system 1900 for use in or with body 1910 immersed adjacent fluid 1905 in which one or more technologies may be implemented. System 1900 may comprise one or more instances of instruction sequences 1916, measurement data 1918 and/or other logic 1930, some or all of which may reside in static or dynamic memory 1920. Such logic 1930 may comprise one or more instances of decision modules 1921, 1922, 1923 or other control modules 1924; timing logic 1925; measurement-responsive logic 1926; configuration modules 1927; or other logic units 1928, 1929. Alternatively or additionally, system 1900 may comprise one or more instances of glucose sensors 1941, inhalation detectors 1942, in situ sense modules, or other sensor modules 1940 as described herein. These and other components of system 1900 may be configured to bear one or more instances of identifiers 1951, 1952 or indications 1961, 1962, such as one or more antennas 1980 or processors 1990 optionally provided therein. In addition to one or more instances of system 1900, body 1910 may comprise one or more ports or other continuous dispensers 1901 (or one or more releasable capsules or other discrete dispensers 1902) configured for dispensing from a bioactive material supply 1907. Body 1910 may likewise comprise one or more ports or other continuous dispensers 1903 (or one or more releasable capsules or other discrete dispensers 1904) configured for dispensing from at least one other bioactive-material-containing supply 1908. As shown, one or more processors may implement a bioactive material selection directly or indirectly, in respective embodiments, by selectively outputting one or more actuator driver outputs 1991, 1992, 1993, 1994 respectively operable for initiating or otherwise controlling dispensation from dispensers 1901-1904 as shown.

In some variants, system 1900 is configured for performing one or more variants of flow 200 (of FIG. 2) described herein. In an embodiment in which antenna 1980 is configured to perform operation 220, for example, antenna 1980 may likewise receive a wireless signal (as signal 1950) indicative of one or more ports, supplies, or other dispensers inside tract 801, for example. In response, one or more decisions module 1921-1923 may (optionally) be configured to signal a decision of which actuator or other dispenser control of a module to activate in response to a received wireless signal.

In light of these teachings, numerous existing techniques may be applied for constructing capsules or other ingestible or releasable structures as described herein without undue experimentation. See, e.g., U.S. Pat. No. 7,182,959 ("Rapidly dissolving dosage form and process for making same"); U.S. Pat. No. 6,962,715 ("Method and dosage form for dispensing a bioactive substance"); U.S. Pat. No. 6,960,356 ("Orally administered drug delivery system providing temporal and spatial control"); U.S. Pat. No. 6,929,636 ("Internal drug dispenser capsule medical device"); U.S. Pat. No. 6,936,279 ("Microcrystalline zeaxanthin with high bioavailability in oily carrier formulations"); U.S. Pat. No. 6,866,863 ("Ingestibles possessing intrinsic color change"); U.S. Pat. No. 6,767,567 ("Ingestible elements"); U.S. Pat. No. 6,703,013 ("Polystyrene sulfonate-containing gel preparation"); U.S. Pat. No. 6,677,313 ("Method for gene therapy using nucleic acid loaded polymeric microparticles"); U.S. Pat. No. 6,475,521 ("Biphasic controlled release delivery system for high solubility pharmaceuticals and method"); U.S. Pat. No. 6,638,533 ("Pulse dosage formulations of methylphenidate and method to prepare same"). Those skilled in the art will also recognize how to apply numerous existing techniques for taking provisional, alternate, overlapping, or completion actions relating to such applications as exemplified herein without undue experimentation, in light of these teachings. Substantially any of these structures or techniques may be used in some form for constructing modules, flow paths, dispensers, or other feature described herein without undue experimentation.

With reference now to FIG. 20, shown is an implantable or ingestible system 2000 suitable for exposure to digestive or other bodily fluid 2065 in which one or more technologies may be implemented. System 2000 may comprise two or more reservoirs 2092, 2093, 2094, 2095, 2096, 2097 operating in a cooperative fashion according to an a priori regimen and/or sensor input or other signals 2041. Such signals may originate from a remote care provider or other external module 2040, for example, optionally after being received locally via a wireless medium. External module 2040 may comprise a wireless router, a radio-frequency identification (RFID) device, and/or a handheld device, for example. Alternatively or additionally, external module 2040 may comprise an article configured to function while worn by a subject, such as a belt or prosthetic device.

One or more such reservoirs 2092-2097 may be configured to separate from the others for dispensation during passage per vias naturales in some embodiments. Alternatively or additionally, one or more others may be configured for selective dispensation via one or more ports 2001, 2002 to respective flow paths as described herein, for example. Such flow paths may pass into an esophagus and/or an intestine, for example, as variously described herein.

As shown, reservoir 2092 may comprise one or more instances of hormones 2017 or other bioactive ingredients and/or carrier materials 2018. Reservoir 2093 may likewise comprise many doses 2032 of a bioactive powder, propellant, or other flowable material. Reservoir 2094 may comprise one or more instances of antimicrobial agents 2073 and/or other bioactive ingredients optionally comprising carrier materials 2078. Reservoir 2097 may comprise a selectable concentration or other mode of dosage 2045, optionally with one or more other instances of ingredients 2051 or other markers 2056. System 2000 may further comprise one or more other compositions 2083, 2084, one or more of which may comprise one or more instances of alkaline materials 2085 or other materials useful for adjusting pH. Optionally some or all such reservoirs may be housed within one or more capsules 2009, optionally at a stable, higher-than-ambient pressure and near-neutral buoyancy. In other variants, however, creases or other hinging structures may be used for coupling respective ones of reservoirs 2092-2097 into one or more ring-like, H-shaped, tetrahedral, or other expanded forms useful for "loitering" for more than a day in a gastric chamber, for example, as described herein.

With reference now to FIG. 21, shown is a system in which one or more technologies may be implemented comprising one or more modules 2100 optionally operable for communication with one or more user interfaces 2110 operable for relaying user output 2116 and/or input 2118. Module 2100 comprises one or more instances of (electrical, electromechanical, software-implemented, firmware-implemented, or other control) devices 2120. Device 2120 may comprise one or more instances of memory 2130; processors 2140; ports 2145, 2146; valves 2151, 2152; antennas 2157; power or other supplies 2158; logic modules 2161, 2162, 2163 or other signaling modules 2160; gauges 2178 or other such active or passive detection components 2170; or piezoelectric transducers 2182, shape memory elements 2183, micro-electromechanical system (MEMS) elements 2184, or other actuators 2180. Such detection components 2170 may comprise one or more instances of sensors 2171 operable for measuring or otherwise detecting a higher-than-nominal concentration of alcohol or other controlled substances, sensors 2172 operable for accepting an indication of or otherwise responding to a proximity to an artificial device from within a portion of the digestive tract, sensors 2173 for measuring or otherwise detecting a higher-than-nominal concentration of an artificial control marker, sensors 2174 operable for measuring or otherwise detecting a higher-than-nominal concentration of lipids, sensors 2175 operable for accepting an indication of or otherwise responding to a pH or other environmental attribute, sensors 2176 operable for measuring or otherwise detecting a higher-than-nominal concentration of carbohydrates or other nutrients, or sensors 2177 operable for accepting an indication of or otherwise responding to a departure of one or more artificial devices from within a specific portion of the digestive tract. Many such devices may be implemented in software or otherwise in memory 2130, such as one or more executable instruction sequences 2132 or supplemental information 2135 as described herein. Alternatively or additionally, in various embodiments, any such devices 2120 may likewise (optionally) handle one or more instances of quantities 2191, 2192; one or more identifiers 2193 or other indications 2194; or other components of messages 2195 or other values 2196, 2197, 2198, 2199 as described herein.

In light of teachings herein, numerous existing techniques may be applied for acquiring or using measurements or other detectable phenomena relating to a digestive tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Many such variations may be implemented in special purpose instructions or code 2132 in memory 2130 or other such components 2170, for example, optionally implemented in special purpose circuitry comprising one or more sensors 2171-2177 or other components 2189 configured for automatic decision making. Combinations of these may each be effectuated by comparative, arithmetic, conjunctive, or other operators relating each pairing of input 2118 or other detectable determinants described with reference to FIG. 21, for example.

In light of teachings herein, numerous existing techniques may be applied for acquiring or using measurements or other detectable phenomena relating to a digestive tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Those skilled in the art will also recognize how to apply numerous existing techniques for taking provisional, alternate, overlapping, or completion actions relating to such decisions as exemplified herein without undue experimentation, in light of these teachings. Such variations may be implemented in instruction sequence 2132 or other implementations of special-purpose logic implementing one or more functions described herein.

In light of these teachings, numerous existing techniques may be applied for directly or indirectly affecting a pH of a local portion of a digestive tract as described herein without undue experimentation. See, e.g., U.S. Pat. No. 7,276,252 ("Method and form of a drug delivery device, such as encapsulating a toxic core within a non-toxic region in an oral dosage form"); U.S. Pat. No. 7,144,877 ("Bile-acid derived compounds for enhancing oral absorption and systemic bioavailability of drugs"); U.S. Pat. No. 7,101,567 ("Controlled release preparations having multi-layer structure"); U.S. Pat. No. 6,926,909 ("Chrono delivery formulations and method of use thereof"); U.S. Pat. No. 6,875,793 ("Once-a-day controlled release sulfonylurea formulation"); U.S. Pat. No. 6,797,268 ("Pharmaceutical composition useful in the treatment of peptic ulcers"); U.S. Pat. No. 6,730,327 ("Polymer blends that swell in an acidic environment and deswell in a basic environment"); U.S. Pat. No. 6,726,924 ("Oral liposomal delivery system"); U.S. Pat. No. 6,764,696 ("Effervescent drug delivery system for oral administration"); U.S. Pat. No. 6,692,771 ("Emulsions as solid dosage forms for oral administration"); U.S. Pat. No. 6,600,950 ("Iontophoretic treatment system"). Those skilled in the art will also recognize how to apply numerous existing techniques for taking provisional, alternate, overlapping, or completion actions relating to such applications as exemplified herein without undue experimentation, in light of these teachings. In some variants, one or more reservoirs or dispensers described herein may comprise a pH-reducing or pH-increasing component in a liquid form, for example, optionally configured for release directly into gastric compartments 170, 870 or other such environments described herein. Alternatively or additionally, such dispensation may be controlled or otherwise informed by one or more sensors 2175 or other components 2170 operable for detecting a pH, a pH change, or one or more other environmental circumstances as designated by a physician or other medical or veterinary professional.

In light of these teachings, numerous existing techniques may be applied for using artificial markers or other diagnostically useful indicator materials as described herein without undue experimentation. See, e.g., U.S. Pat. No. 7,256,398 ("Security markers for determining composition of a medium"); U.S. Pat. No. 7,252,932 ("Methods for the detection, analysis and isolation of nascent proteins"); U.S. Pat. No. 7,238,471 ("Method of diagnosing, monitoring, staging, imaging and treating breast cancer"); U.S. Pat. No. 7,228,159

("Optical sensor containing particles for in situ measurement of analytes"); U.S. Pat. No. 7,202,045 ("Detection and treatment of cancers of the lung"); U.S. Pat. No. 7,198,756 ("Noninvasive measurement of pH"); U.S. Pat. No. 7,118,919 ("13C glucose breath test for the diagnosis of diabetic indications and monitoring glycemic control"); U.S. Pat. No. 7,118,912 ("Methods and compositions for categorizing patients"); U.S. Pat. No. 7,105,300 ("Sequencing by incorporation")"); U.S. Pat. No. 7,070,937 ("Marker useful for detection and measurement of free radical damage and method"); U.S. Pat. No. 6,977,068 ("Method for detection of fibrin clots"); U.S. Pat. No. 6,905,884 ("Fluorescent cobalamins and uses thereof"); U.S. Pat. No. 6,703,045 ("Composition and method for maintaining blood glucose level"); U.S. Pat. No. 6,753,135 ("Biological markers for evaluating therapeutic treatment of inflammatory and autoimmune disorders"); U.S. Pat. No. 6,680,172 ("Treatments and markers for cancers of the central nervous system"); U.S. Pat. No. 6,628,982 ("Internal marker device for identification of biological substances"); U.S. Pat. No. 6,585,646 ("Screening test and procedure using skin patches"); U.S. Pat. No. 6,534,323 ("Compositions and methods for early detection of heart disease"); U.S. Pat. No. 6,500,625 ("Methods for diagnosing cancer or precancer based upon hnRNP protein expression"); U.S. Pat. No. 6,419,896 ("Non-invasive approach for assessing tumors in living animals"); U.S. Pat. No. 5,639,656 ("Antibodies reactive with biological markers of benign prostate hyperplasia"). Those skilled in the art will also recognize how to apply numerous existing techniques for taking provisional, alternate, overlapping, or completion actions relating to such applications as exemplified herein without undue experimentation, in light of these teachings. One or more ports 2145, 2146, valves 2151, 2152, pumps, or other actuators may likewise be used for selecting among two or more bioactive mixtures or other materials, one or more of which may include such marking ingredients.

Referring gain to FIG. 11, in some variants, tethers described herein may comprise one or more instances of soluble portions 1103 accessible by fluid 1165 only when exposed by an activation of one or more piezoelectric transducers 2182, shape-memory element 2183, springs, or other actuators 2180. One or more such actuators 2180 may open or otherwise control one or more valves 2151, 2152 selectively in response to components 2170 as described herein, for example. Alternatively or additionally, one or more instances of tethers 1108 may comprise middle portion 1104 at least some of which is semi-soluble or substantially insoluble in one or more digestive fluids 1165 in a typical stomach or other intended environments.

In an embodiment in which system 1100 comprises more than three modules 1110 each small enough to pass through a specific digestive tract, a "fourth" one of modules 1110 may (optionally) engage at least one end (e.g. distal portion 1109) of tether 1108. Alternatively or additionally, in many applications, modules 1110 may be few enough, inert enough, or otherwise implemented on a small enough scale so that their one or more dispensers 1150 may be operable for dispensing a total of at most 15 grams of medicinal material. A fraction of modules 1110 may lack dispensers, for example, especially if configured for one or more other specialty functions. System 1100 may implement a version of tethered group 1090 as described herein, for example, in which module 1092 is inflatable, in which module 1093 comprises one or more implementations of device(s) 2120 operable for external communication, in which module 1094 includes one or more actuators 2180 operable for severing or otherwise manipulating tether 1098, in which module 1095 comprises one or more cameras or other components 2170 operable for data capture, and/or in which module 1096 performs one or more other resource-intensive specialty functions. Such systems 1100 may be assembled from inventories of diverse-looking modules 1010, 1020, 1030, 1040 within a local care facility, for example, based upon information available just before deployment into a digestive tract.

Figure 22:
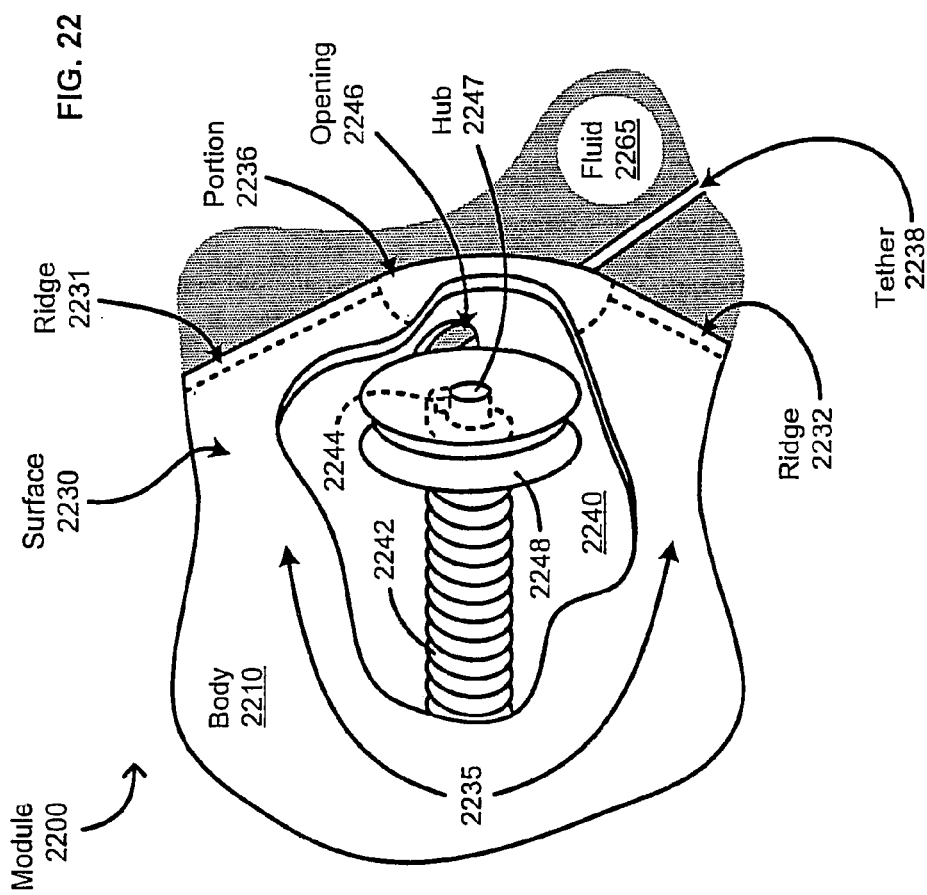

With reference now to FIG. 22, shown is an example of a system that may serve as a context for introducing one or more processes and/or devices described herein. As shown system module 2200 may include at least one unitary body 2210 having an external surface 2230 comprising at least one convex portion 2236, at least one saddle region 2235, at least two (at least partly convex) ridge regions 2231, 2232, and at least one opening 2246. A cutaway reveals chamber 2240 within module 2200 containing at least one spool 2248 operable to retract a (rotationally symmetric or asymmetric) portion of tether 2238 by rotating about hub 2247. Metallic or other deformable windings 2242 are pre-loaded (under tension, e.g.) so that spool 2248 is urged counter-clockwise (as shown), which torque is initially resisted by one or more soluble or semi-soluble latches 2244. When body 2210 is immersed enough so that suitable digestive or other fluid 2265 enters chamber 2240, however, fluid 2265 dissolves the latch(es) 2244, freeing spool 2248 to draw in 1% or more of (the length of) tether 2238.

Figure 23:
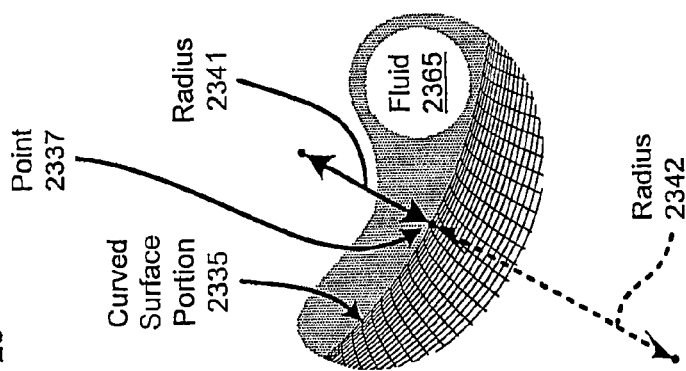

With reference now to FIG. 23, shown is an example of a curved surface portion 2335 that may serve as a context for introducing one or more processes and/or devices described herein. Curved surface portion 2335 defines a saddle region, one in which each point 2337 has an outer (e.g. upper side, facing fluid 2365) radius 2341 of curvature in one plane and an inner (e.g. lower side) radius 2342 of curvature in an orthogonal plane.

Figure 24:
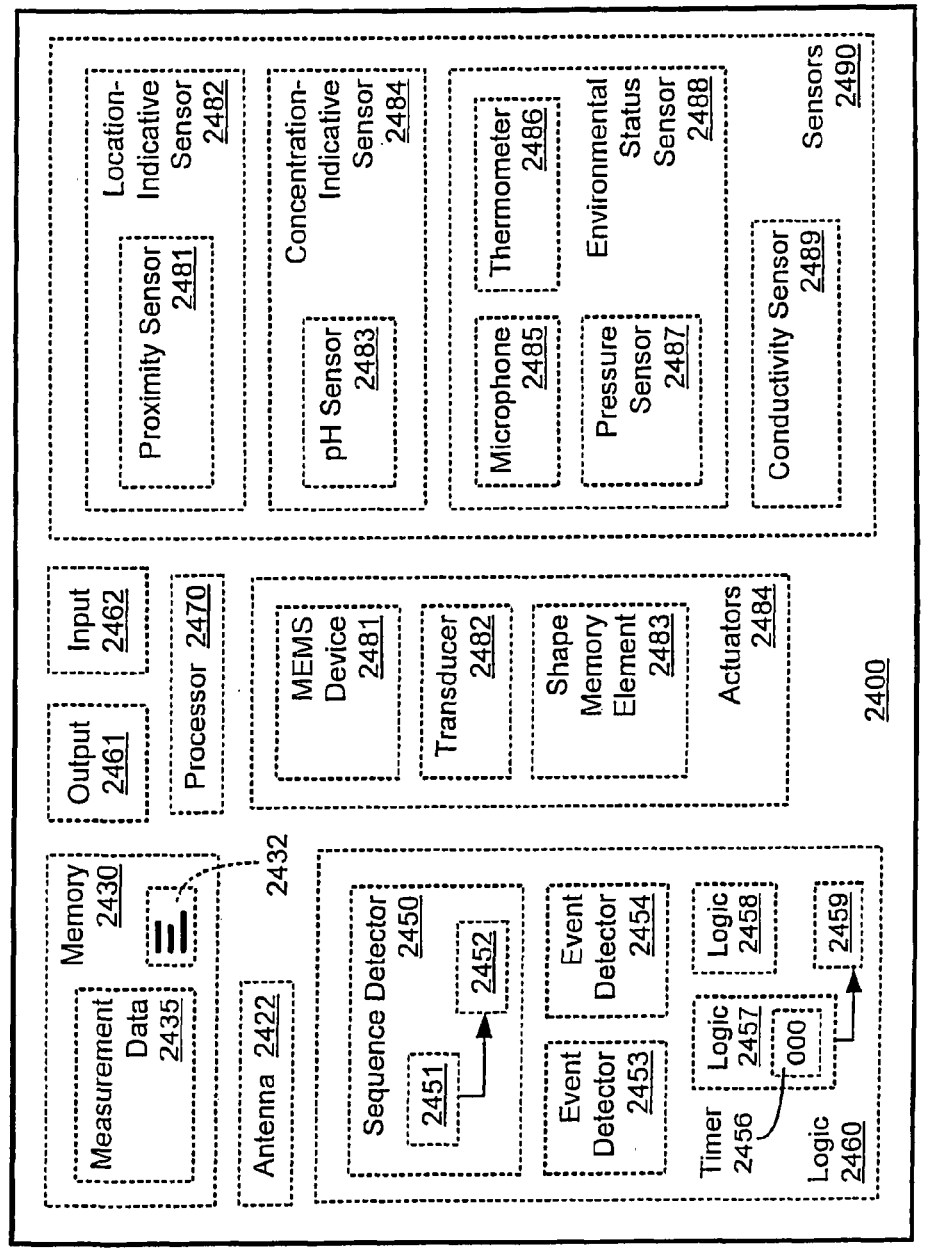

With reference now to FIG. 24, shown is an example of a system that may serve as a context for introducing one or more processes and/or devices described herein. As shown system 2400 may include one or more instances of antennas 2422, memory 2430, logic 2460, output 2461, input 2462, processors 2470, actuators 2484, or sensors 2490. Memory 2430 may comprise one or more instances of instruction sequences 2432 or measurement data 2435. Logic 2460 include one or more instances of sequential functions 2451, 2452 or other components of sequence detectors 2450; event detectors 2453, 2454; timers 2456 or other logic 2457, 2458, 2459 implemented in hardware or software, for example. Actuators 2484 may comprise one or more instances of MEMS devices 2481, transducers 2482, shape memory elements 2484, or other microfluidic or other components suitable for use in situ. See, e.g., FIG. 5. Sensors 2490 may comprise one or more instances of proximity sensors 2481 or other location-indicative sensors 2482; pH sensors 2483 or other concentration-indicative sensors 2484; microphones 2485, thermometers 2486, pressure sensors 2487, or other environmental status sensors 2488; conductivity sensors 2489; or other sensors as described herein or in documents identified above.

Figure 25:
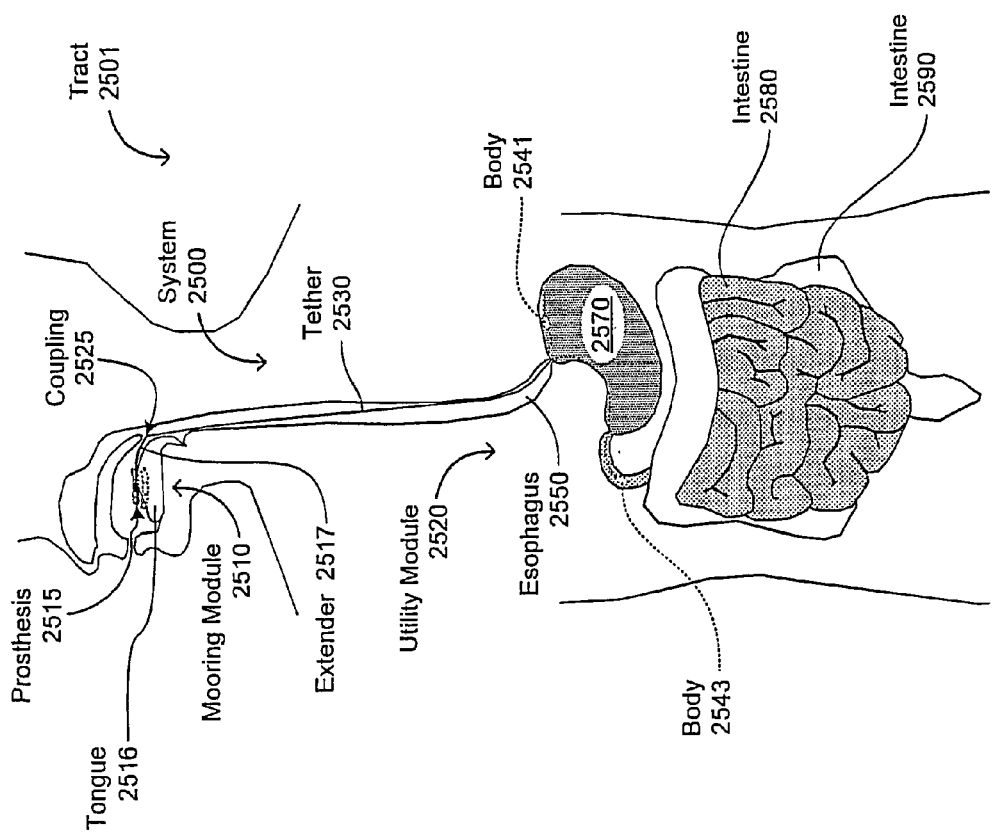

With reference now to FIG. 25, shown is a digestive tract 2501 in a vicinity of which one or more technologies may be implemented. System 2500 may comprise one or more utility modules 2520 supported by one or more mooring modules 2510. Mooring module 2510 may, for example, comprise one or more prostheses 2515 supported at least partly by an upper portion of the subject's mouth, as shown, supporting at least an adaptable extender 2517 (over and/or beside tongue 2516, as shown) which supports one or more tethers 2530 via coupling 2525. The utility module(s) 2520 may, in various embodiments, comprise one or more bodies 2541, 2543 in esophagus 2550, gastric compartment 2570, or intestines 2580, 2590.

Body 2541 may comprise a primary material supply operable for placement within gastric compartment 2570, for example. Such bodies 2541 may occur, for example, in embodiments in which one or more tethers 2530 comprise conduits operable to guide material from the primary material supply out of the stomach. Alternatively or additionally, one or more such tethered or other bodies 2541, 2543 may comprise one or more sensors or other devices in substantially any of the variants described above.

In light of teachings herein, and referring again to FIGS. 1 & 3, those skilled in the art will recognize that any of the above-described dispensers may (optionally) be configured for use in or with a body having one or more protruding surfaces 375 overlapping one or more binding agent secretion ports 301, 302 as described herein (or as in documents identified above). Alternatively or additionally, one or more such secretion ports may likewise provide one or more therapeutic ingredients as described herein or in documents identified above.

Referring again to FIG. 4, any of the above-described systems may (optionally) communicate with or include one or more instances of optical communication elements 410 effective for interacting with one or more utility modules 450 from a position at least partly outside the digestive tract. Such external modules may likewise include one or more instances of radio frequency or other communication elements effective for interacting with one or more utility modules 450 from a position at least partly outside the digestive tract. Any of the above-described modules may likewise include one or more instances of wireless-control components 451-453 operable to remain in an engaging state for longer than a day, week, or other period consistent with a programmatic dosing and/or observation program as described herein or in documents identified above.

Any of the above-described physical modules may likewise include one or more instances of ferromagnetic element(s) 460 or other flux-guiding elements 1026 (exemplified at FIG. 10). Alternatively or additionally, such modules may likewise include one or more instances of conductive coil 471 in some embodiments, such as for carrying a current at least partly in opposition to a magnetic field generated by ferromagnetic element(s) 460, and optionally for carrying a current spike sufficient for demagnetizing ferromagnetic element(s) 460 at least partially.

Referring again to FIG. 5, any of the above-described physical modules may likewise include one or more instances of disengagement-inducing actuators 581 or control circuitry 591 therefor, optionally operable for providing a separation force sufficient to compensate at least partly for adhesion, magnetic attraction, and/or other coupling features as described herein or in documents identified above. Such control circuitry 591 may be configured to operate in response to one or more wireless signals or other conditions signifying or invoking a regimen completion or other disengagement function, for example, as described herein.

Any of the above-described physical modules may likewise include one or more instances of releasable dispensers 589 or reservoirs, dispenser-releasing actuators 582, and control circuitry 592 therefor responsive to detected conditions as described herein or in documents identified above. Such control circuitry 592 may be configured to operate in response to one or more wireless signals or other conditions signifying or invoking a physician-specified dispenser release function, for example, as described herein.

Any of the above-described physical modules may likewise include one or more instances of reservoir-opening actuators 583 and control circuitry 593 therefor. Such control circuitry 593 may be configured to operate in response to one or more wireless signals or other conditions signifying or invoking a predetermined or updated reservoir-opening function, for example, as described herein.

Any of the above-described therapeutic dispensers may likewise include one or more instances of dosage-adjustment actuators 585 or control circuitry 595 therefor responsive to detected conditions as described herein or in documents identified above. Such control circuitry 595 may be configured to operate in response to one or more wireless signals or other conditions signifying or invoking a physician-specified dosage adjustment function, for example, as described herein. Alternatively or additionally, such dispensers may be configured for continuous dispensation throughout a period of more than an hour, day, or month, for example, through one or more conduits extending from or through a gastric compartment.

Any of the above-described physical modules may likewise include one or more instances of adhesive-containing dispensers 564 (optionally containing liquid binding agents as described herein or other adhesives) and control circuitry 574 therefor. Such control circuitry 574 may be configured to operate in response to one or more wireless signals or other conditions signifying or invoking a predetermined or updated adhesive-dispensation function, for example, as described herein.

Any of the above-described physical modules may likewise include one or more instances of adhesive-solvent-containing dispensers 565 and control circuitry 575 therefor. Such control circuitry 575 may be configured to operate in response to one or more wireless signals or other conditions signifying or invoking a predetermined or updated solvent-dispensation function, for example, as described herein.

Any of the above-described physical modules may likewise include one or more instances of anticoagulant-agent-containing dispensers 566 and control circuitry 576 therefor. Such control circuitry 576 may be configured to operate in response to one or more wireless signals or other conditions signifying or invoking a physician-specified anticoagulant-agent-dispensation function, for example, as described herein.

Any of the above-described physical modules may likewise include one or more instances of antibiotic-containing dispensers 567 and control circuitry 577 therefor. Such control circuitry 577 may be configured to operate in response to one or more wireless signals or other conditions signifying or invoking a subject-specific antibiotic-agent-dispensation function, for example, as described herein.

Referring again to FIG. 6, any of the above-described physical modules may likewise include one or more instances of bodies having (a) ports 601 or other initial attachment features and/or (b) ports 602 or other attachment features configured for taking effect soe time later later. In some variants, for example, one or both of these features may include piercing or gripping elements, magnetic elements, adhesive elements, elements suitable to be acted upon, or otherwise as described herein.

Referring again to FIG. 19, any of the above-described physical modules may likewise include one or more instances configuration modules 1926, components 2170 in hardware and/or software, or other portions of system 1900 configured for implementing one or more condition detection criterion updates, for example.

In contexts of FIGS. 21-24, for example, such updates may be received directly as input 2118 from a physician. Any of the above-described modules may likewise include one or more instances of pH sensors 2483 or other sensors 2170, 2484 operable for detecting one or more acidity-indicative or other material-concentration-indicative conditions to which control circuitry or other circuitry described herein may be responsive as described herein or in documents identified above. Any of the above-described modules may likewise include one or more instances of microphones 2485, thermometers 2486, pressure sensors 2487, or other environmental status sensors 2488. Alternatively or additionally, any such modules may include one or more instances of MEMS devices 2481, shape memory elements 2483, or other actuators 2484.

Any of the above-described modules may likewise include one or more instances of logic module 2162 or other circuitry operable for transmitting measurement data from one or more sensors 2170 or related supplemental information 2135 via a wireless signal. Alternatively or additionally, such device(s) 2120 may include one or more valves 2151 operable for controlling material flow to one or more corresponding binding agent secretion ports 2145 and/or one or more valves 2152 operable for controlling material flow to one or more other binding agent secretion ports 2146.

Any of the above-described modules may likewise include one or more instances of saddle regions 2235 overlapping a mucous membrane and/or deformable windings 2242 or other actuators suitable for moving some of one or more adaptable extender modules.

Referring again to FIGS. 18 & 20, any of the above-described modules may likewise include one or more instances of operable reservoirs 2092-2097 or other material dispensers 1821, 1826, any of which may contain one or more instances of anti-inflammatory agents, appetite suppressants, hormones 2017, anti-hyperglycemic-medications, antimicrobial agents, nutrients, propellants or other fluids, polymer-containing or other binding agents, or any combinations of these or other ingredients 2051 as described herein. Alternatively or additionally, such ingredients 2051 may include buffered, diluted, curable, or other component or composite materials. Alternatively or additionally, one or more such reservoirs 2097 may comprise one or more dosages 2045 of microbes, inoculants, or other organic materials and/or complex structures pursuant to a physician-specified course of treatment.

Any of the above-described modules may likewise include one or more instances of reservoirs 2093 or other supply containing two or more doses 2032 of such therapeutic materials, each such dose including about 10 milligrams or more of a hormone or other active ingredient 2051 as described herein. Such reservoirs may likewise constitute or complement one or more instances of reservoirs or other supplies containing a total of about 10 grams or more of an antimicrobial agent 2073 or other active ingredient 2051 as described herein.

Any of the above-described flow paths may likewise include one or more instances of narrowed and/or serpentine sections, counters, or other elements suitable for inducing a nominal delay, typically on the order of a minute, of an hour, or of a week. Any of the above-described modules may likewise include one or more instances of tethers 1830, extenders 1217 (of FIG. 12), or other support structures bearing one or more anesthetic agents, optionally having a portion to be positioned on or near an airway-membrane.

Referring again to FIG. 12, any of the above-described systems may likewise comprise one or more instances of mooring modules 1210, 2510, or some other component able to support itself in a subject comprising one or more tethers 2530 or other adaptable portions 1221, 1222 each about 3 to 30 centimeters or longer. Such modules may likewise comprise one or more orthodontic prostheses 2515 or other rigid modules operable to support such adaptable portions. Alternatively or additionally, such modules may comprise one or more adhesive materials operable for coupling at least to a mucous membrane and for supporting at least one of the one or more adaptable extender modules.

Referring again to FIGS. 18-20, those skilled in the art will appreciate that component modules 1896, 1897 or other "modules" described herein may implement one or more reservoirs 2092-2097 and/or one or more described attributes of body 1910, as described above. Any such module may likewise implement one or more devices 2120, logic 1930, or other attributes of an electrical or other system as described below. In light of teachings herein, numerous existing techniques may be applied for forming or assembling components of modules suitable for use in various portions of a digestive tract for various functions as described herein without undue experimentation. See, e.g., U.S. Pat. No. 7,182,957 ("Polymer blends that swell in an acidic environment and deswell in a basic environment"); U.S. Pat. No. 7,097,851 ("Oral formulation for gastrointestinal drug delivery"); U.S. Pat. No. 7,041,083 ("Medical catheter assembly including a removable inner sleeve and method of using the same"); U.S. Pat. No. 6,797,283 ("Gastric retention dosage form having multiple layers"); U.S. Pat. No. 6,120,803 ("Prolonged release active agent dosage form adapted for gastric retention"); U.S. Pat. No. 5,198,229 ("Self-retaining gastrointestinal delivery device"); U.S. Pat. No. 4,522,625 ("Drug dispenser comprising wall formed of semipermeable member and enteric member"); U.S. Pat. Pub. No. 2007/0178160 ("Gastro-intestinal device and method for treating addiction"); U.S. Pat. Pub. No. 2007/0106213 ("Gastrointestinal applicator and method of using same"); U.S. Pat. Pub. No. 2006/0068003 ("System for increasing compliance with medication regime"); U.S. Pat. Pub. No. 2005/0249799 ("Polymeric drug delivery system for hydrophobic drugs"); U.S. Pat. Pub. No. 2005/0201974 ("Bioadhesive polymers with catechol functionality"); U.S. Pat. Pub. No. 2005/0058701 ("Active drug delivery in the gastrointestinal tract"); U.S. Pat. Pub. No. 2004/0224019 ("Oral controlled release system for targeted drug delivery into the cell and its nucleus for gene therapy, DNA vaccination, and administration of gene based drugs"); U.S. Pat. Pub. No. 2004/0109894 ("pH triggered targeted controlled release systems for the delivery of pharmaceutical active ingredients"); U.S. Pat. Pub. No. 2003/0232078 ("Formulation & dosage form for the controlled delivery of therapeutic agents"); U.S. Pat. Pub. No. 2003/0113371 ("Composition and method for maintaining blood glucose level by employing the hydrophilic matrix based oral controlled release antidiabetic composition"). Those skilled in the art will also recognize how to apply numerous existing techniques for taking provisional, alternate, overlapping, or completion actions relating to such decisions as exemplified herein without undue experimentation, in light of these teachings. Such variations may be typically be implemented with existing manufacturing techniques in light of these teachings.

In some variants in which module 2100 implements system 1900, system 1900 may comprise one or more ports 2145 or other components operable for interaction with processor 1990 or other circuitry for implementing a bioactive material selection from within a digestive tract as described herein, including one or more valves 2151 configured to operate within gastric compartment 870. Alternatively or additionally, system 1900 may likewise be configured to include or otherwise communicate with one or more other valves 820 (of FIG. 8), 2152 or dispensers 1821 configured to operate outside gastric compartment 870. In some variants, for example, one or more dispensers 1904 may be configured to release one or more fluid antibiotics or the like continuously from supply 1908 into a subject's intestine, once triggered by processor 1990 (e.g. by actuator driver output 1994).

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A medical or veterinary system comprising:
    a module body small enough for a subject to swallow;
    an earlier-acting attachment feature operable for coupling the module body to a first portion of a mucous membrane, the earlier-acting attachment feature including at least:
        one or more attachment elements including at least one of a piercing element, a gripping element, a magnetic-flux-guiding element, or an adhesive material;
        a first delay-inducing element responsive to an apparent ingestion of the module body;
        a first actuator operable for coupling the module body to the first portion of the mucous membrane at least partially using the one or more attachment elements; and
    a later-acting attachment feature operable for coupling the module body to a second portion of the mucous membrane at least one minute after the earlier-acting attachment feature couples the module body to the first portion of the mucous membrane, the later-acting attachment feature including at least:
        a second delay-inducing element that is slower than the first delay-inducing element by at least an hour; and
    the later-acting attachment feature including at least a second actuator operable for injecting a polymer-containing binding agent into a binding location suitable for coupling the module body to the second portion of the mucous membrane responsive to the second delay-inducing element.

2. The medical or veterinary system of claim 1 in which the module body further comprises:
    one or more sensors.

3. The medical or veterinary system of claim 1 in which the module body further comprises:
    one or more anti-hyperglycemic-medication-containing reservoirs.

4. The medical or veterinary system of claim 1 in which the module body further comprises:
    one or more appetite-suppressant-containing reservoirs.

5. The medical or veterinary system of claim 1 in which the module body further comprises:
    at least some of the earlier-acting attachment feature.

6. The medical or veterinary system of claim 1 in which the earlier-acting attachment feature further comprises:

circuitry for invoking at least the first actuator operable for coupling the module body to the first portion of the mucous membrane responsive to an apparent ingestion of the module body.

7. The medical or veterinary system of claim 1 in which the later-acting attachment feature comprises:

circuitry for invoking at least the second actuator operable for coupling the module body to the second portion of the mucous membrane.

8. The medical or veterinary system of claim 1 in which the later-acting attachment feature comprises:

one or more binding agent secretion ports.

9. The medical or veterinary system of claim 1, further comprising:

a carrier at least partly supporting the module body and one or more other bodies.

10. The medical or veterinary system of claim 1, further comprising:

a tether.

11. The medical or veterinary system of claim 1, further comprising:

another attachment feature operable for engaging the mucous membrane.

12. The medical or veterinary system of claim 1 in which the earlier-acting attachment feature further comprises:

circuitry for invoking at least the first actuator responsive to the first delay-inducing element.

13. The medical or veterinary system of claim 12 in which the module body further comprises:

a sensor-containing module that includes at least one or more of a carbohydrate sensor or a pH sensor; and a reservoir containing a therapeutic material that includes at least one or more of an appetite suppressant or an anti-hyperglycemic-medication.

14. A medical or veterinary system comprising:

a sensor-containing module that includes at least one or more of a carbohydrate sensor or a pH sensor;

a reservoir containing a therapeutic material that includes at least one or more of an appetite suppressant or an anti-hyperglycemic-medication;

an earlier-acting attachment feature that includes one or more attachment elements operable for coupling the sensor-containing module to a first portion of a mucous membrane;

a first delay-inducing element responsive to apparent ingestion of the sensor-containing module;

a second delay-inducing element being slower than the first delay-inducing element by at least an hour; and a later-acting attachment feature including at least an actuator operable for injecting a polymer-containing binding agent into a binding location suitable for coupling the sensor-containing module to a portion of the mucous membrane responsive to the second delay-inducing element.

15. The medical or veterinary system of claim 14 in which the earlier-acting attachment feature comprises:

one or more attachment elements including at least one of a piercing element, a gripping element, a magnetic-flux-guiding element, or an adhesive material.

16. The medical or veterinary system of claim 14 in which the sensor-containing module further comprises:

at least some of the earlier-acting attachment feature.

17. The medical or veterinary system of claim 14 in which the later-acting attachment feature comprises:

one or more binding agent secretion ports.

18. The medical or veterinary system of claim 14, further comprising:

a carrier at least partly supporting the sensor-containing module and one or more other bodies.

19. The medical or veterinary system of claim 14, further comprising:

a tether.

20. The medical or veterinary system of claim 14, further comprising:

another attachment feature operable for engaging the mucous membrane.

\* \* \* \* \*